US007220716B2

(12) United States Patent
Estell

(10) Patent No.: US 7,220,716 B2
(45) Date of Patent: May 22, 2007

(54) PROTEASES FROM GRAM-POSITIVE ORGANISMS

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 249 days.

(21) Appl. No.: 10/927,590

(22) Filed: Aug. 25, 2004

(65) Prior Publication Data

US 2005/0059112 A1    Mar. 17, 2005

Related U.S. Application Data

(60) Division of application No. 09/932,183, filed on Aug. 17, 2001, now Pat. No. 6,833,265, which is a continuation of application No. 09/308,375, filed as application No. PCT/US98/18828 on Sep. 8, 1998, now Pat. No. 6,300,117.

(30) Foreign Application Priority Data

Oct. 13, 1998  (GB) ................................ 9719636.4

(51) Int. Cl.
C11D 3/386    (2006.01)
A23K 1/165    (2006.01)
D06M 16/00    (2006.01)
C12N 9/54     (2006.01)

(52) U.S. Cl. .................... 510/300; 435/263; 435/69.1; 435/219; 435/320.1; 426/53

(58) Field of Classification Search ..................... None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,261,868 A | 4/1981 | Hora et al. |
| 4,275,149 A | 6/1981 | Litman et al. |
| 4,277,437 A | 7/1981 | Maggio |
| 4,366,241 A | 12/1982 | Tom et al. |
| 4,404,128 A | 9/1983 | Anderson |
| 4,533,359 A | 8/1985 | Kondo et al. |
| 4,816,567 A | 3/1989 | Cabilly et al. |
| 5,147,642 A | 9/1992 | Lotz et al. |
| 5,204,015 A | 4/1993 | Caldwell et al. |
| 5,264,366 A | 11/1993 | Ferrari et al. |
| 5,314,692 A | 5/1994 | Haarasilta et al. |
| 5,612,055 A | 3/1997 | Bedford et al. |

FOREIGN PATENT DOCUMENTS

| | | |
|---|---|---|
| EP | 0134267 | 8/1989 |
| EP | 0 369 817 A | 5/1990 |
| WO | WO 95/14099 | 5/1995 |

OTHER PUBLICATIONS

*Altschul, Stephen F. et al., << Basic Local Alignment Search Tool , >> J. Mol. Biol. 215: 403-410, 1990.
*Anagnostopoulos, C. et al., << Requirements for Transformation In Bacillus subtilis, >> J. Bacteriol., 81:741-746, 1961.
21634 4/1982 RD.
*Bakhiet, Nouna et al., << Studies on Transfection and Transformation of Protoplasts of Bacillus larvae, Bacillus subtilis, and Bacillus popilliae, >> Appl. Envrion. Microbiol., vol. 49, No. 3, pp. 577-581, 1985.
*Benton, W. David et al., << Screening λgt Recombinant Clones by Hybridization to Single Plaques in situ, >> Science, 196:180-182, 1977.
*Chang, Shing et al., << High Frequency Transformation of Bacillus subtilis Protoplasts by Plasmid DNA, >> Mol. Gen. Genet. 168:111-115, 1979.
*Contente, Sara et al., << Marker Rescue Transformation by Linear Plasmid DNA in Bacillus subtilis, >> Plasmid, 2 :555-571, 1979.
*EMBL/GENBANK Databases Accession No. 031976 (1988).
*EMBL/GENBANK Databases Accession No. AF020713 (1988).
*Fischer, Hans-Martin et al., << Introduction of plasmid pC194 into Bacillus thuringiensis by protoplast transformation and plasmid transfer, >> Arch. Microbiol., 139:213-217, 1984.
*Grunstein, Michael et al., << Colony hybridization : A method for the isolation of cloned DNAs that contain a specific gene, >> Proc. Natl. Acad. Sci. U.S.A., 72:3961, 1975.
*Halma, Peter et al., << Novel plasmid marker rescue transformation system for molecular cloning in Bacillus subtilis enabling direct selection of recombinants, >> Mol. Gen. Genet. 223 :185-191, 1990.
*Holubova, I. et al., << Transfer of Liposome-Encapsulated Plasmid DNA to Bacillus subtilis Protoplasts and Calcium-Treated Escherichia coli Cells, >> Folia Microbiol., vol. 30, pp. 97-100, 1985.
*Kroll, David J. et al., << A Multifunctional Prokaryotic Protein Expression System: Overproduction, Affinity Purification, and Selective Detection, >> DNA Cell Biol., vol. 12, No. 5, pp. 441-453, 1993.
*Kunst, F. et al., << The Complete genome sequences of a Gram-positive bacterium Bacillus subtilis, >> Nature, vol. 390, pp. 249-256, 1997.
*Maddox, D.E. et al., << Elevated Serum Levels in Human Pregnancy of a Molecule Immunochemically Similar to Eosinophil Granule Major Basic Protein, >> J. Exp. Med., vol. 158, pp. 1211-1226, Oct. 1983.

(Continued)

Primary Examiner—Nashaat T. Nashed
Assistant Examiner—William W. Moore

(57) ABSTRACT

The present invention relates to the identification of novel metallo-proteases (MP) in Gram-positive microorganisms. The present invention provides the nucleic acid and amino acid sequences for Bacillus (MP). The present invention also provides host cells having mutation or deletion of part or all of the gene encoding MP. The present invention also provides host cells further comprising nucleic acid encoding desired heterologous proteins such as enzymes. The present invention also provides cleaning compositions comprising an MP of the present invention.

4 Claims, 31 Drawing Sheets

OTHER PUBLICATIONS

*Mann, Stephen P. et al., << Transformation of *Bacillus* spp.: an Examination of the Transformation of *Bacillus* Protoplasts by Plasmids pUB110 and pHV33,>> Current Microbiol., vol. 13, pp. 191-195, 1986.

*McDonald, Karen Orzech et al., << Plasmid Transformation of *Bacillus sphaericus* 1593,>> J. General Microbiology, vol. 130, pp. 203-208, 1984.

*Murray, Elizabeth E., << Codon usage in plant genes, >> Nucleic Acids Research, vol. 17, No. 2, pp. 477-498, 1989.

*Ogasawara, Naotake et al., << Systematic sequencing of the *Bacillus subtilis* genome : progress report of the Japanese group, >> Microbiology, vol. 141, pp. 257-259, 1995.

*Porath, Jerker, << Immobilized Metal Ion Affinity Chromatography, >> Protein Expression and Purification, 3 :263-281, 1992.

*Smith, Michael D. et al., << Protoplast Transformation in Coryneform Bacteria and Introduction of an α-Amylase Gene from *Bacillus amyloliquefaciens* into *Brevibacterium lactofermentum*, >> Applied and Environmental Microbiology, 51:634-639, 1986.

*Vorabjeva, I.P. et al., << Transformation of *Bacillus megaterium* Protoplasts by Plasmid DNA, >> FEMS Microbiology Letters, 7:261-263, 1980.

*Weinrauch, Y. et al., << Plasmid Marker Rescue Transformation in *Bacillus subtilis*, >> J. Bacteriol. 154 :1077-1087, 1983.

*Weinrauch, Y. et al., << Plasmid Marker Rescue Transformation Proceeds by Breakage-Reunion in *Bacillus subtilis*, >> Journal of Bacteriology, 169 :1205-1211, 1987.

Lazarevic V. et al., "Nucleotide Sequence of the Bacillus Subtllis Temperate Bacteriophage SPbetac2", *Microbiology*, vol. 145, pp. 1055-1087 (1999).

ATATTGGCATGGGTGTTATGGATGTAATTATTAAGAAAGCAAACAAAGTCGCTCAATAACT
    |         |         |         |         |         |       60
TATAACCGTACCACATACCTACATTAATAATTCTTTGTTTCAGCGAGTTATTGA

GAGTGGCTTTTTTCTTTGTCCCTCTCCCCTACTGAAAGGAAGTGATTCTTACTTGAGTCAA
    |         |         |         |         |         |      120
CTCACCGAAAAAGAAACAGGAGAGGGGATGACTTTCCTTCACTAAGAATGAACTCAGTT
                                                    Leu Ser Gln
                                                      └─Yoml──

AACCTCAAAATTATACTAACCCCGCAAGCTGATACCTCATCCAAAACTGTCGAACAGTTA
    |         |         |         |         |         |      180
TTGGAGTTTTAATATGATTGGGGCGTTCGACTATGGAGTAGGTTTTGACAGCTTGTCAAT
Asn Leu Lys Ile Ile Leu Thr Pro Gln Ala Asp Thr Ser Ser Lys Thr Val Glu Gln Leu
                                     └─────────Yoml─────────────────────────

AATCAGCAAATTAAAATCCCTGGAAAAGAAACTCAACTTCAAGCTCAATACAAACATT
    |         |         |         |         |         |      240
TTAGTCGTTTAATTTTAGGGACCTTTTCTTTGAGTTGAAGTTCGAGTTATGTTTGTAA
Asn Gln Gln Ile Lys Ser Leu Glu Lys Lys Leu Asn Ser Leu Lys Leu Asn Thr Asn Ile
                                                └────────Yoml──────────────

FIG._1A-1

```
GATTCTACAACCTTAAAAGCTCTGCAAGAATTCTCCTCTGCTATCGACACATATCAGAAA
                                                              300
CTAAGATGTTGGAATTTTCGAGACGTTCTTAAGAGGAGACGATAGCTGTGTATAGTCTTT

Asp Ser Thr Leu Lys Ala Leu Gln Glu Phe Ser Ser Ala Ile Asp Thr Tyr Gln Lys
                                                              Yoml AACCTAAAATCCTATAATCAAACAGTTAAAGAACCTCAACAGTAATTAAGAATGCTGAC
                                                              360
TTGGATTTTAGGATATTAGTTTGTCAATTTCTTGGAGTTGTCATTAATTCTTACGACTG Asn Leu Lys Ser Tyr Asn Gln Thr Val Lys Glu Thr Ser Thr Val Ile Lys Asn Ala Asp
                                                              Yoml GGATCAGTTGAAAAGCTCACCCAGCAGTATAAGAAAAATGGTGAGATACTTCAACGTGAA
                                                              420
CCTAGTCAACTTTTCGAGTGGGTCGTCATATTCTTTTTACCACTCTATGAAGTTGCACTT Gly Ser Val Glu Lys Leu Thr Gln Gln Tyr Lys Lys Asn Gly Glu Ile Leu Gln Arg Glu
                                                              Yoml ACAAAAAATAATCAACAATCGTAATACAGCATTAAAGCAAGAAACTCAAGAGGTTAACAAG
                                                              480
TGTTTTTATTAGTTGTTAGCATTATGTCGTAATTTCGTTCTTTGAGTTCTCCAATTGTTC Thr Lys Ile Ile Asn Asn Arg Asn Thr Ala Leu Lys Gln Glu Thr Gln Glu Val Asn Lys
                                                              Yoml
```

FIG._1A-2

```
CTAACACAGGCCACTGAGAAACTAGGACAGGTTCAAAAAAGACTGTGCAGAGAAATCTG
      |         |         |         |         |         |        540
GATTGTGTCCGGTGACTCTTTGATCCTGTCCAAGTTTTTTCTGACACGTCTCTTTAGAC

Leu Thr Gln Ala Thr Glu Lys Leu Gly Gln Val Gln Lys Lys Thr Val Gln Arg Asn Leu
                                         Yoml CAAGGACAGCCAACAAAGGTAGTGCAGAGAAAAACCGCCACGGGTTCGATGATATTGTTTAT
      |         |         |         |         |         |        600
GTTCCTGTCGGTTGTTCCATCACGTCTCTTTTTGGCGGTGCCCAAGCTACTATAACAAATA Gln Gly Gln Pro Thr Lys Val Val Gln Lys Asn Arg His Gly Phe Asp Asp Ile Val Tyr
                                         Yoml ACAACTGATCCTAAAACTAATTCGACCTCCTCAAAAACTACAACTAATTATGACCAACAA
      |         |         |         |         |         |        660
TGTTGACTAGGATTTTGATTAAGCTGGAGGAGTTTTGATGTTGATTAATACTGGTTGTT Thr Thr Asp Pro Lys Thr Asn Ser Thr Thr Ser Ser Lys Thr Thr Asn Tyr Asp Gln Gln
                                         Yoml AGGAGAGCAATTGAGCAGCTTAAGCAAGATTTAGAGAAGCTTAGACAGCAAGGTATTGTT
      |         |         |         |         |         |        720
TCCTCTCGTTAACTCGTCGAATTCGTTCTAAATCTCTTCGAATCTGTCGTTCCATAACAA Arg Arg Ala Ile Glu Gln Leu Lys Gln Asp Leu Glu Lys Leu Arg Gln Gln Gly Ile Val
```

FIG._1B-1

```
ACTGATACGACCATCCATCTCTTGGCCGAAAATAAACACAGCTCAATCCGCTCAACAA
    |         |         |         |         |         |       780
TGACTATGCTGGTAGAGTAGAGAACCGGCTTTTATTTGTCGAGTTAGGCGAGTTGTT

Thr Asp Thr Thr Ile Ser Ser Leu Gly Arg Lys Ile Asn Thr Ala Gln Ser Ala Gln Gln
                                   Yoml
```

```
ATTGAAGCACTGCAAAATAGGATAAGGATGTTAGAGATGATAAATCTGCGGCAGTTGCGAAG
    |         |         |         |         |         |       840
TAACTTCGTGACGTTTTATCCTATTCCTACAATCTCTACTATTTAGACGCCGTCAACGCTTC

Ile Glu Ala Leu Gln Asn Arg Ile Arg Met Leu Asp Asp Lys Ser Ala Ala Val Ala Lys
                                   Yoml
```

```
AACAATGAATTAAAAGAAAACCATTGAATTATATCAGGCGACAGGCACAAGTAAAATGTTCAA
    |         |         |         |         |         |       900
TTGTTACTTAATTTTCTTTTGGTAACTTAATATAGTCGCTGTCCGTGTTCATTTACAAGTT

Asn Asn Glu Leu Lys Lys Thr Ile Glu Leu Tyr Gln Arg Gln Ala Gln Val Asn Val Gln
                                   Yoml
```

FIG._1B-2

```
AACCTAAATACACGGTATGGCAGTTCTATGGGCTCTAGTAATAGACAAGCTGTTCAAGAT
----+----+----+----+----+----+----+----+----+----+----+----+ 960
TTGGATTTATGTGCCATACCGTCAAGATACCCGAGATCATTATCTGTTCGACAAGTTCTA

Asn Leu Asn Thr Arg Tyr Gly Ser Ser Met Gly Ser Ser Asn Arg Gln Ala Val Gln Asp
                                              Yoml TATTTGAATGCAGTAAATAGTCTTAATGTAAGCACTGGAAGCAATAATATCAGATCACAA
----+----+----+----+----+----+----+----+----+----+----+----+ 1020
ATAAACTTACGTCATTTATCAGAATTACATTCGTGACCTTCGTTATTATAGTCTAGTGTT Tyr Leu Asn Ala Val Asn Ser Leu Asn Val Ser Thr Gly Ser Asn Asn Ile Arg Ser Gln
                                            Yoml ATTCAAAGCTTGAATATGCAATTTAGAGAATTAGCCTCCAACGCTCAAACAGCTGCTAAT
----+----+----+----+----+----+----+----+----+----+----+----+ 1080
TAAGTTTCGAACTTATACGTTAAATCTCTTAATCGGAGGTTGCGAGTTTGTCGACGATTA Ile Gln Ser Leu Asn Met Gln Phe Arg Glu Leu Ala Ser Asn Ala Gln Thr Ala Ala Asn
                                                   Yoml CAAGCCCTCTCTTTTGGGAGCAGAACTAACCCAAAACCTTCAAAAGCATGTCCACCTATTTA
----+----+----+----+----+----+----+----+----+----+----+----+ 1140
GTTCGGAGAAGAAAACCCTCGTCTTGATTGGGTTTGGAAGTTTTCGTACAGGTGGATAAAT Gln Ala Ser Ser Phe Gly Ala Glu Leu Thr Gln Thr Phe Lys Ser Met Ser Thr Tyr Leu
                                                 Yoml
```

FIG._1C-1

```
ATCTCCGGTTCTTTATTCTACGGAGCTATCTCTGGACTTAAAGAAATGGTATCCCAGGCA
----+----+----+----+----+----+----+----+----+----+----+----+    1200
TAGAGGCCAAGAAATAAGATGCCTCGATAGAGACCTGAATTTCTTTACCATAGGGTCCGT

Ile Ser Gly Ser Leu Phe Tyr Gly Ala Ile Ser Gly Leu Lys Glu Met Val Ser Gln Ala
                                       Yoml ATAGAAATTGATACTCTCATGACAAATATTCGCCGTGTTATGAATGAGCCGGATTATAAA
----+----+----+----+----+----+----+----+----+----+----+----+    1260
TATCTTTAACTATGAGAGTACTGTTTATAAGCGGCACAATACTTACTCGGCCTAATATTT Ile Glu Ile Asp Thr Leu Met Thr Asn Ile Arg Arg Val Met Asn Glu Pro Asp Tyr Lys
                                       Yoml TATAATGAACTTCTCCAAGAATCTATTGACTTAGGTGATACACTTTCAAATAAAATCACA
----+----+----+----+----+----+----+----+----+----+----+----+    1320
ATATTACTTGAAGAGGTTCTTAGATAACTGAATCCACTATGTGAAAGTTTATTTTAGTGT Tyr Asn Glu Leu Leu Gln Glu Ser Ile Asp Leu Gly Asp Thr Leu Ser Asn Lys Ile Thr
                                       Yoml GATATTCTTCAAATGACAGGCGATTTTGGGAGAATGGGTTTCGATGAAAGTGAGCTCTCC
----+----+----+----+----+----+----+----+----+----+----+----+    1380
CTATAAGAAGTTTACTGTCCGCTAAAACCCTCTTACCCAAAGCTACTTTCACTCGAGAGG Asp Ile Leu Gln Met Thr Gly Asp Phe Gly Arg Met Gly Phe Asp Glu Ser Glu Leu Ser
                                       Yoml
```

FIG. _1C-2

```
ACGTTAACGACGAAAACTGCCCAAGTTCTTCAAAATGTCTCTGATTTAACTCCCGATGATACA    1440
     |         |         |         |         |         |
TGCAATTGCTTTTGACGGGTTCAAGAAGTTTTACAGAGACTAAATTGAGGGCTACTATGT

Thr Leu Thr Lys Thr Ala Gln Val Leu Gln Asn Val Ser Asp Leu Thr Pro Asp Asp Thr
                                    Yoml
```

```
GTTAACACTCTAACGGCAGCAATGCTCAACTTTAATATTGCAGCAAATGATTCAATATCA    1500
     |         |         |         |         |         |
CAATTGTGAGATTGCCGTCGTTACGAGTTGAAATTATAACGTCGTTACTAAGTTATAGT

Val Asn Thr Leu Thr Ala Ala Met Leu Asn Phe Asn Ile Ala Ala Asn Asp Ser Ile Ser
                                    Yoml
```

```
ATTGCAGATAAATTAAATGAGGTTGATAATAACTATGCTGTTACAACTCTAGATCTGGCC    1560
     |         |         |         |         |         |
TAACGTCTATTTAATTTACTCCAACTATTATTGATACGACAATGTTGAGATCTAGACCGG

Ile Ala Asp Lys Leu Asn Glu Val Asp Asn Asn Tyr Ala Val Thr Thr Leu Asp Leu Ala
                                    Yoml
```

```
AATTCTATCCGTAAAGCTGGTTCAACTGCTTCTACATTCGGGGTAGAGCTAAATGATCTT    1620
     |         |         |         |         |         |
TTAAGATAGGCATTTCGACCAAGTTGACGAAGATGTAAGCCCCATCTCGATTTACTAGAA

Asn Ser Ile Arg Lys Ala Gly Ser Thr Ala Ser Thr Phe Gly Val Glu Leu Asn Asp Leu
                                    Yoml
```

FIG.–1D-1

```
ATTGGTTATACAACTGCAATTGCTAGTACAACACGTGAATCAGGGAATATCGTCGGGAAC
     +         +         +         +         +         + 1680
TAACCAATATGTTGACGTTAACGATCATGTTGTGCACTTAGTCCCTTATAGCAGCCCTTG

Ile Gly Tyr Thr Thr Ala Ile Ala Ser Thr Arg Glu Ser Gly Asn Ile Val Gly Asn
                                  —————Yoml—————

TCCTTAAAGACAATTTTCGCGGGATTGGGAATAATCAGCTCAATTAAAGGCGTTAGAA
     +         +         +         +         +         + 1740
AGGAATTTCTGTTAAAAGCGCCCTAACCCTTATTAGTTCGAGTTAATTTCGCAATCTT

Ser Leu Lys Thr Ile Phe Ala Arg Ile Gly Asn Asn Gln Ser Ser Ile Lys Ala Leu Glu
                                          Yoml CAGATTGGTATCTCAGTTAAAAACAGCTGGTGGTGAAGCTAAATCAGCAAGTGATTTAATT
     +         +         +         +         +         + 1800
GTCTAACCATAGAGTCAATTTTTGTCGACCACCACTTCGATTTAGTCGTTCACTAAATTAA Gln Ile Gly Ile Ser Val Lys Thr Ala Gly Gly Glu Ala Lys Ser Ala Ser Asp Leu Ile
                                          Yoml AGTGAAGTTGCTGGTAAGTGGGATACGCTTTCTGATGCTCAGAAACAAAATACTTCAATT
     +         +         +         +         +         + 1860
TCACTTCAACGACCATTCACCCTATGCGAAAGACTACGAGTCTTTGTTTTATGAAGTTAA Ser Glu Val Ala Gly Lys Trp Asp Thr Leu Ser Asp Ala Gln Lys Gln Asn Thr Ser Ile
                                          Yoml
```

FIG.—1D-2

```
GGAGTAGCTGGTATTTATCAATTATCCCGTTTTAATGCAATGATGAACAACTTCTCTATT
         +         +         +         +         +         +     1920
CCTCATCGACCATAAATAGTTAATAGGGCAAATTACGTTACTACTTGTTGAAGAGATAA
 Gly Val Ala Gly Ile Tyr Gln Leu Ser Arg Phe Asn Ala Met Met Asn Asn Phe Ser Ile
                                                        Yoml GCTCAGAATGCGGGCTAAAACTGCGGCTAACTCAACAGGAAGTGCTTGGAGTGAGCAGCAA
         +         +         +         +         +         +     1980
CGAGTCTTACGCCCGATTTTGACGCCGATTGAGTTGTCCTTCACGAACCTCACTCGTCGTT
 Ala Gln Asn Ala Ala Lys Thr Ala Ala Asn Ser Thr Gly Ser Ala Trp Ser Glu Gln Gln
                          Yoml AAGTATGCAGATAGTCTACAAGCTAGGGTAAATAAGCTTCAAAATAACTTCACTGAATTT
         +         +         +         +         +         +     2040
TTCATACGTCTATCAGATGTTCGATCCCATTTATTCGAAGTTTTATTGAAGTGACTTAAA
 Lys Tyr Ala Asp Ser Leu Gln Ala Arg Val Asn Lys Leu Gln Asn Asn Phe Thr Glu Phe
                              Yoml GCTATTGCAGCTTCTGATGCTTTTATTAGCGACGGATTAATTGAATTACTCAAGCCGCA
         +         +         +         +         +         +     2100
CGATAACGTCGAAGACTACGAAAATAATCGCTGCCTAATTAACTTAATGAGTTCGGCGT
 Ala Ile Ala Ala Ser Asp Ala Phe Ile Ser Asp Gly Leu Ile Glu Phe Thr Gln Ala Ala
                          Yoml
```

FIG._1E-1

```
GGTTCTTTGCTTAACGGCTTCTACAGGAGTAATCAAATCAGTTGGGTTCCTACCTCCCTT
----+----+----+----+----+----+----+----+----+----+----+----+  2160
CCAAGAAACGAATTGCGAAGATGTCCTCATTAGTTAGTCAACCCAAGGATGGAGGGGAA
 Gly Ser Leu Leu Asn Ala Ser Thr Gly Val Ile Lys Ser Val Gly Phe Leu Pro Pro Leu
                                                    └──Yoml──────────────────

TTAGCTGCAGTAAGCACTGCAACCCTTTTGCTCAGTAAGAATACCGCACATTAGCCAGC
----+----+----+----+----+----+----+----+----+----+----+----+  2220
AATCGACGTCATTCGTGACGTTGGGAAAACGAGTCATTCTTATGGCGTGTAATCGGTCG
 Leu Ala Ala Val Ser Thr Ala Thr Leu Leu Ser Lys Asn Thr Arg Thr Leu Ala Ser
                                                    └──Yoml──────────────────

AGCCTAATTTTGGGCACACGTGCAATGGGCAAGAAACTTTAGCGACTGCTGGGCTAGAA
----+----+----+----+----+----+----+----+----+----+----+----+  2280
TCGGATTAAAACCCGTGTGCACGTTACCCGTTCTTTGAAATCGCTGACGACCCGATCTT
 Ser Leu Ile Leu Gly Thr Arg Ala Met Gly Gln Glu Thr Leu Ala Thr Ala Gly Leu Glu
                                                    └──Yoml──────────────────

GCTGGTATGACTCGTGTGCAGCAGTCGCCTCAAGAGTTCTAAAAACTGCTCTTCGAGGGTTG
----+----+----+----+----+----+----+----+----+----+----+----+  2340
CGACCATACTGAGCACGTCGTCAGCGGAGTTCTCAAGATTTTTGACGAGAAGCTCCCAAC
 Ala Gly Met Thr Arg Ala Ala Val Ala Ser Arg Val Leu Lys Thr Ala Leu Arg Gly Leu
                                                    └──Yoml──────────────────
```

FIG._1E-2

```
CTTGTTTCAACTTTAGTTGGGCGGTGCATTTGCTCTGCTTTGGGATGGGCGCTAGAATCATTA
     ----+----+----+----+----+----+----+----+----+----+----+----+    2400
GAACAAAGTTGAAATCAACCGCCACGTAAACGACGAAACCCTACCCGCGATCTTAGTAAT

Leu Val Ser Thr Leu Val Gly Gly Ala Phe Ala Ala Leu Gly Trp Ala Leu Glu Ser Leu
                                                  Yoml ATTTCTCTTTTGCAGAAGCTAAAAAGCTAAAAAAGATGATTTGAGCAGAGCCAGCAAACC
     ----+----+----+----+----+----+----+----+----+----+----+----+    2460
TAAAGAGAAAACGTCTTCGATTTTTCGATTTTCTACTAAAACTCGTCTCGGTCGTTTGG Ile Ser Ser Phe Ala Glu Ala Lys Lys Asp Asp Phe Glu Gln Ser Gln Gln Thr
                                            Yoml AATGTCGAAGCAATTACGACCAATAAAGACTCCACTGATAAACTAATACAGCAATATAAA
     ----+----+----+----+----+----+----+----+----+----+----+----+    2520
TTACAGCTTCGTTAATGCTGGTTATTCTGAGGTGACTATTTGATTATGTCGTTATATTT Asn Val Glu Ala Ile Thr Thr Asn Lys Asp Ser Thr Asp Lys Leu Ile Gln Gln Tyr Lys
                                                  Yoml GAGCTTCAAAAAGTTAAAGAGTCAAGATCTTAACTTCAGATGAAGAGCAAGAATACCTT
     ----+----+----+----+----+----+----+----+----+----+----+----+    2580
CTCGAAGTTTTTCAATTTCTCAGTTCTAGAAATTGAAGTCTACTTCTCGTTCTTATGGAA Glu Leu Gln Lys Val Lys Glu Ser Arg Ser Leu Thr Ser Asp Glu Glu Gln Glu Tyr Leu
                                            Yoml
```

FIG._1F-1

```
CAAGTCACTCAGCAATTAGCACAAACTTTCCCTGCATTAGTTAAAGGCTATGATTCTCAA
   ----+----+----+----+----+----+----+----+----+----+----+----+   2640
GTTCAGTGAGTCGTTAATCGTGTTGAAAGGGACGTAATCAATTCCGATACTAAGAGTT
 Gln Val Thr Gln Gln Leu Ala Gln Thr Phe Pro Ala Leu Val Lys Gly Tyr Asp Ser Gln
                                          Yoml
```
```
GGAAATGCAATTCTTAAGACAAATAAAGAGCTTGAAAAAGCGATTGAGAATACTAAAGAG
   ----+----+----+----+----+----+----+----+----+----+----+----+   2700
CCTTTACGTTAAGAATTCTGTTTATTTCTCGAACTTTTTCGCTAACTCTTATGATTTCTC
 Gly Asn Ala Ile Leu Lys Thr Asn Lys Glu Leu Glu Lys Ala Ile Glu Asn Thr Lys Glu
                                      Yoml
```
```
TATTTGGCTTTAAAGAAACAAGAGAAACAAGCAGCCAAAGAAAACATTCGAAGACGCT
   ----+----+----+----+----+----+----+----+----+----+----+----+   2760
ATAAACCGAAATTTCTTGTTCTCTTTGTTCGTCGGCGTTCTTTTGTAAGCTTCTGCGA
 Tyr Leu Ala Leu Lys Lys Gln Glu Thr Arg Asp Ser Ala Lys Lys Thr Phe Glu Asp Ala
                                              Yoml
```
```
TCTAAGGAAATTAAAAAGTCTAAGGATGAATTAAAGCAGTACAAACAAATAGCTGACTAC
   ----+----+----+----+----+----+----+----+----+----+----+----+   2820
AGATTCCTTTAATTTTTCAGATTCCTACTTAATTTCGTCATGTTTGTTTATCGACTGATG
 Ser Lys Glu Ile Lys Lys Ser Lys Asp Glu Leu Lys Gln Tyr Lys Gln Ile Ala Asp Tyr
                                          Yoml
```

*FIG._1F-2*

```
AACGATAAAGGTAGACCTAAATGGATCTCTCATTGCAGAGATGACGATGACTATAAGGTTGCA
                                                                    2880
TTGCTATTTCCATCTGGATTTACCCTAGAGTAACGTCTACTGCTACTGATATTCCAACGT

Asn Asp Lys Gly Arg Pro Lys Trp Asp Leu Ile  Ala Asp Asp Asp Tyr Lys Val Ala
                                                  Yoml
```

```
GCTGATAAAGCTAAACAAGTATGCTCAAAGCTCAATCTGACATTGAGAGTGGAAATGCT
                                                                    2940
CGACTATTTCGATTTGTTCATACGAGTTTCGAGTTAGACTGTAACTCTCACCTTTACGA

Ala Asp Lys Ala Lys Gln Ser Met Leu Lys Ala Gln Ser Asp Ile Glu Ser Gly Asn Ala
                                                          Yoml
```

```
AAAGTTAAAGATAGCGTCCTTTCAATTGCAAATGCTTATAGTTCAATTGATATCAGTAAT
                                                                    3000
TTTCAATTTCTATCGCAGGAAAGTTAACGTTTACGAATATCAAGTTAACTATAGTCATTA

Lys Val Lys Asp Ser Val Leu Ser Ile  Ala Asn Ala Tyr Ser Ser Ile Asp Ser Asn
                                                          Yoml
```

```
ACTTTAAAGACGAGTATTAGTGATGTGTCAACAAACTTAAC-TAAAAGATGATTTAGAT
                                                                    3060
TGAAATTTCTGCTCATAATCACTACAACAGTTGTTTGAATTGAATTGAATTTTCTACTAAATCTA

Thr Leu Lys Thr Ser Ile Ser Asp Val Val Asn Lys Leu Asn Leu Lys Asp Asp Leu Asp
                                                          Yoml
```

FIG._1G-1

```
CCTGAAGAATTAGAAAAATTCTCCTCTTCTTTAGGAAAGCTTCAAGAAAAAATGCAAAAA
     +         +         +         +         +         +       3120
GGACTTCTTAATCTTTTTAAGAGGAGAAGAATCCTTTCGAAGTTCTTTTTACGTTTTT
 Pro Glu Leu Glu Lys Phe Ser Ser Leu Gly Lys Leu Gln Glu Lys Met Gln Lys
                                                              Yoml GCTTTAGATTCAGGGGATGAAAAAGCTTTCGATAACGCAAAAAAAGATCTTCAAAGTCTC
     +         +         +         +         +         +       3180
CGAAATCTAAGTCCCCTACTTTTTCGAAAGCTATTGCGTTTTTTCTAGAAGTTTCAGAG
 Ala Leu Asp Ser Gly Asp Glu Lys Ala Phe Asp Asn Ala Lys Lys Asp Leu Gln Ser Leu
                                          Yoml TTGGAAACATACTCCAAATCCGATTCTTCTATTGATGTTTTTAAAAATGAGCTTCGACAAA
     +         +         +         +         +         +       3240
AACCTTTGTATGAGGTTTAGGCTAAGAAGATAACTACAAAAATTTTACTCGAAGCTGTTT
 Leu Glu Thr Tyr Ser Lys Ser Asp Ser Ser Ile Asp Val Phe Lys Met Ser Phe Asp Lys
                                                              Yoml GCACAGAAGAACATAAAAGATGGAGATAAGAGCTTATCTTCCGTCAAATCTGAAGTTGGT
     +         +         +         +         +         +       3300
CGTGTCTTCTTGTATTTTCTACCTCTATTCTCGAATAGAAGGCAGTTTAGACTTCAACCA
 Ala Gln Lys Asn Ile Lys Asp Gly Asp Lys Ser Leu Ser Ser Val Lys Ser Glu Val Gly
                                    Yoml
```

FIG.–1G-2

```
GATTTAGGTGAGACGCTGGCAGAAGCAGGTAACGAGGCAGAAGATTTTGGTAAGAAGCTA
        +         +         +         +         +         +    3360
CTAAATCCACTCTGCGACCGTCTTCGTCCATTGCTCCGTCTTCTAAAACCATTCTTCGAT

Asp Leu Gly Glu Thr Leu Ala Glu Ala Gly Asn Glu Ala Glu Asp Phe Gly Lys Lys Leu
                                                Yoml AAGAAGAGCTCTGGATGCAAATAGTGTTGATGATATTAAGGCAGCTATTAAAGAAATGTCA
        +         +         +         +         +         +    3420
TTCTTCGAGACCTACGTTTATCACAACTACTATAATTCCGTCGATAATTCTTTACAGT Lys Glu Ala Leu Asp Ala Asn Ser Val Asp Asp Ile Lys Ala Ala Ile Lys Glu Met Ser
                                                Yoml GATGCTATGCAGTTCGATTCCGTTCAAGATGTCTTAAATGGGATATATTTTAATAACACC
        +         +         +         +         +         +    3480
CTACGATACGTCAAGCTAAGGCAAGTTCTACAGAATTTACCCCTATAAAAATTATTGTGG Asp Ala Met Gln Phe Asp Ser Val Gln Asp Val Leu Asn Gly Asp Ile Phe Asn Asn Thr
                                                Yoml AAAGATCAAGTAGCTCCTCTCAATGATCTTCTGGAAAAAATGGCTGAAGGTAAAAGTATT
        +         +         +         +         +         +    3540
TTTCTAGTTCATCGAGGAGAGTTACTAGAAGACCTTTTTACCGACTTCCATTTTCATAA Lys Asp Gln Val Ala Pro Leu Asn Asp Leu Leu Glu Lys Met Ala Glu Gly Lys Ser Ile
                                                Yoml
```

FIG. _ 1H-1

```
TCTGCAAATGAAGCTAATACCCTTATTCAAAAAGATAAGGAACTTGCCCAGGCTATTAGC
     ----+----|----+----|----+----|----+----|----+----|----+----|  3600
AGACGTTTACTTCGATTATGGGAATAAGTTTTTCTATTCCTTGAACGGGTCCGATAATCG

Ser Ala Asn Glu Ala Asn Thr Leu Ile Gln Lys Asp Lys Glu Leu Ala Gln Ala Ile Ser
                                                                 ─── Yoml ───

ATCGAAAAATGGCGTTGTGAAATTAACCGTGATGAAGTTATCAAACAAAGAAAAGTTAAA
     ----+----|----+----|----+----|----+----|----+----|----+----|  3660
TAGCTTTTTACCGCAACACTTTAATTGGCACTACTTCAATAGTTTGTTTCTTTTCAATTT

Ile Glu Asn Gly Val Val Lys Ile Asn Arg Asp Glu Val Ile Lys Gln Arg Lys Val Lys
─────────────────────────────── Yoml ───────────────────────────

CTTGATGCTTATAACGACATGGTTACCTACAGCAATAAATTGATGAAAACAGAAGTTAAC
     ----+----|----+----|----+----|----+----|----+----|----+----|  3720
GAACTACGAATATTGCTGTACCAATGGATGTCGTTATTTAACTACTTTTGTCTTCAATTG

Leu Asp Ala Tyr Asn Asp Met Val Thr Tyr Ser Asn Lys Leu Met Lys Thr Glu Val Asn
─────────────────────────────── Yoml ───────────────────────────

AACGCTATCAAAACTTTAAAACGCTGATACCTTACGGATTGACAGCCTGAAAAAGCTACGA
     ----+----|----+----|----+----|----+----|----+----|----+----|  3780
TTGCGATAGTTTTGAAATTTTGCGACTATGGAATGCCTAACTGTCGGACTTTTTCGATGCT

Asn Ala Ile Lys Thr Leu Asn Ala Asp Thr Leu Arg Ile Asp Ser Leu Lys Lys Leu Arg
─────────────────────────────── Yoml ───────────────────────────
```

FIG._1H-2

```
AAAGAACGAAAGCTTGATATGTCTGAGGCCGAACTGTCAGACCTAGAAGTTAAGTCAATT
------+---------+---------+---------+---------+---------+   3840
TTTCTTGCTTTCGAACTATACAGACTCCGGCTTGACAGTCTGGATCTTCAATTCAGTTAA
Lys Glu Arg Lys Leu Asp Met Ser Glu Ala Glu Leu Ser Asp Leu Glu Val Lys Ser Ile
                                                     ──YomI──

AATAATGTTGCAGATGCAAAAAAAGAACTTAAAAAGCTTGAAGAGAAAATGCTTCAACCT
------+---------+---------+---------+---------+---------+   3900
TTATTACAACGTCTACGTTTTTTCTTGAATTTTCGAACTTCTCTTTTACGAAGTTGGA
Asn Asn Val Ala Asp Ala Lys Lys Glu Leu Lys Lys Leu Glu Glu Lys Met Leu Gln Pro
                                            ──YomI──

GGTGGATACTCCAATAGTCAAATTGAAGCAATGCAAAAGCGTTAAATCAGCTTTAGAATCT
------+---------+---------+---------+---------+---------+   3960
CCACCTATGAGGTTATCAGTTTAACTTCGTTACGTTTCGCAATTTAGTCGAAATCTTAGA
Gly Gly Tyr Ser Asn Ser Gln Ile Glu Ala Met Gln Ser Val Lys Ser Ala Leu Glu Ser
                                                ──YomI──

TATATTTCTGCATCTGAAGAAGCCACCAGTACACAAGAAATGAATAAACAGGCACTTGTT
------+---------+---------+---------+---------+---------+   4020
ATATAAAGACGTAGACTTCTTCGGTGGTCATGTGTTCTTTACTTATTTGTCCGTGAACAA
Tyr Ile Ser Ala Ser Glu Glu Ala Thr Ser Thr Gln Glu Met Asn Lys Gln Ala Leu Val
                                        ──YomI──
```

FIG._1I-1

```
GAAGCTGGAACATCATTGGAGAATCAACAAGAGAAAAGCCAATGAAGAAACC
----+----+----+----+----+----+----+----+----+----+----+----+  4080
CTTCGACCTTGTAGTAACCTCTTAACCTGTCTAGTTGTTCTTTTTCGGTTACTTCTTTGG

Glu Ala Gly Thr Ser Leu Glu Asn Trp Thr Asp Gln Gln Glu Lys Ala Asn Glu Glu Thr
                                                    Yoml AAGACTTCCATGTATGTTGTTGATAAATACAAGGAAGCATTAGAAAAAGTTAATGCTGAG
----+----+----+----+----+----+----+----+----+----+----+----+  4140
TTCTGAAGGTACATACAACAACTATTATGTTCCTTCGTAATCTTTTCAATTACGACTC Lys Thr Ser Met Tyr Val Val Asp Lys Tyr Lys Glu Ala Leu Glu Lys Val Asn Ala Glu-
                                                              Yoml ATTGACAAGTACAACAAGCAGGTCAATGATTATCCTAAATACTCTCAGAAATATCGAGAT
----+----+----+----+----+----+----+----+----+----+----+----+  4200
TAACTGTTCATGTTGTCGTCCAGTTACTAATAGGATTATGAGAGTCTTTATAGCTCTA Ile Asp Lys Tyr Asn Lys Gln Val Asn Asp Tyr Pro Lys Tyr Ser Gln Lys Tyr Arg Asp
                                                              Yoml GCAATCAAGAAAGAAATTAAAGCACTTCAGCAAAAGAAAAAGCTTATGCAGGAACAAGCT
----+----+----+----+----+----+----+----+----+----+----+----+  4260
CGTTAGTTCTTTCTTTAATTTCGTGAAGTCGTTTTCTTTTTCGAATACGTCCTTGTTCGA Ala Ile Lys Lys Glu Ile Lys Ala Leu Gln Gln Lys Lys Lys Leu Met Gln Glu Gln Ala
                                                              Yoml
```

FIG._11-2

```
AAGCTGCTTAAAGATCAAATTAAATCCGGTAACATTACTCAATACGGTATTGTAACCTCT
————————+————————+————————+————————+————————+————————+  4320
TTCGACGAATTTCTAGTTTAATTTAGGCCATTGTAATGAGTTATGCCATAACATTGGAGA
 Lys Leu Leu Lys Asp Gln Ile Lys Ser Gly Asn Ile Thr Gln Tyr Gly Ile Val Thr Ser
                                                   Yoml ACAACTTCTTCTGGTGAACCCCCTCCTCAACTGGTGGATCATATTCAGGCAAGTATTCA
————————+————————+————————+————————+————————+————————+  4380
TGTTGAAGAAGACCACCTTGGGGGAGGAGTTGACCACCTAGTATAAGTCCGTTCATAAGT
 Thr Thr Ser Ser Gly Gly Thr Pro Ser Ser Thr Gly Gly Ser Tyr Ser Gly Lys Tyr Ser
                                              Yoml AGCTACATAAATTCAGCAGCTAGTAAATACAATGTTGACCCTGCCCTTATTGCAGCTGTA
————————+————————+————————+————————+————————+————————+  4440
TCGATGTATTTAAGTCGTCGATCATTTATGTTACAACTGGGACGGGAATAACGTCGACAT
 Ser Tyr Ile Asn Ser Ala Ala Ser Lys Tyr Asn Val Asp Pro Ala Leu Ile Ala Ala Val
                                                  Yoml ATTCAGCAAGAATCAGGGGTTTAATGCTAAAGCACGATCTGGTGTAGGTGCCATGGGATTA
————————+————————+————————+————————+————————+————————+  4500
TAAGTCGTTCTTAGTCCCAAATTACGATTTCGTGCTAGACCACATCCACGGTACCCTAAT
 Ile Gln Gln Glu Ser Gly Phe Asn Ala Lys Ala Arg Ser Gly Val Gly Ala Met Gly Leu
                                                   Yoml
```

FIG._1J-1

```
ATGCAACTGATGCCAGCAACAGCAAAAAGCTTAGGAGTAAATAACGCTTACGATCCTTAT
----+----+----+----+----+----+----+----+----+----+----+----+  4560
TACGTTGACTACGGTCGTCGTTTTTCGAATCCTCATTTATTGCGAATGCTAGGAATA
 Met Gln Leu Met Pro Ala Thr Ala Lys Ser Leu Gly Val Asn Asn Ala Tyr Asp Pro Tyr
                                     Yoml CAAAATGTTATGGGTGGAACAAAGTACCTCGCCCAACAACTTGAAAAAGTTTGGGGTAAT
----+----+----+----+----+----+----+----+----+----+----+----+  4620
GTTTTACAATACCCACCTTGTTTCATGGAGCGGGTTGTTGAACTTTTTCAAACCGCCATTA
 Gln Asn Val Met Gly Gly Thr Lys Tyr Leu Ala Gln Gln Leu Glu Lys Phe Gly Gly Asn -
                                     Yoml GTTGAAAAAGCATTGGCTGCATATAATGCTGGGCCTGGTAACGTAATTAAATATGGTGGT
----+----+----+----+----+----+----+----+----+----+----+----+  4680
CAACTTTTTCGTAACCGACGTATATTACGACCCGGACCATTGCATTAATTATACCACCA
 Val Glu Lys Ala Leu Ala Ala Tyr Asn Ala Gly Pro Gly Asn Val Ile Lys Tyr Gly Gly
                                     Yoml ATCCCTCCTTTTAAAGAAACACAGAATTACGTCAAGAAGATCATGGCCAACTATAGCAAA
----+----+----+----+----+----+----+----+----+----+----+----+  4740
TAGGGAGGAAAATTTCTTTGTGTCTTAATGCAGTTCTTCTAGTACCGGTTGATATCGTTT
 Ile Pro Pro Phe Lys Glu Thr Gln Asn Tyr Val Lys Lys Ile Met Ala Asn Tyr Ser Lys
                                     Yoml
```

FIG._1J-2

```
TCGCTCTCTCATCTGCCACTTCTTCAATCGCCAGCTATTATACAAATAATAGCGCTTTTAGG
----+----+----+----+----+----+----+----+----+----+----+----+ 4800
AGCGAGAGTAGACGGTGAAGAAGTTAGCCGGTCGATAATATGTTATTATCGCGAAAATCC

Ser Leu Ser Ser Ala Thr Ser Ser Ile Ala Ser Tyr Tyr Thr Asn Asn Ser Ala Phe Arg
                                      Yoml GTAAGCTCCAAATATGGACAACAGGAATCTGGTCTCCGCTCCTCCCCACACAAAGGAACT
----+----+----+----+----+----+----+----+----+----+----+----+ 4860
CATTCGAGGTTTATACCTGTTGTCCTTAGACCAGAGGCGAGGAGGGGTGTGTTTCCTTGA Val Ser Ser Lys Tyr Gly Gln Gln Glu Ser Gly Leu Arg Ser Ser Pro His Lys Gly Thr
                                      Yoml GATTTTGCTGCAAAAGCAGGTACAGCAATTAAATCTCTTCAAAGTGGTAAAGTCCAAATT
----+----+----+----+----+----+----+----+----+----+----+----+ 4920
CTAAAACGACGTTTTCGTCCATGTCGTTAATTTAGAGAAGTTTCACCATTTCAGGTTTAA Asp Phe Ala Ala Lys Ala Gly Thr Ala Ile Lys Ser Leu Gln Ser Gly Lys Val Gln Ile
                                      Yoml GCTGGCTACAGTAAAACTGCAGGTAACTGGGTTGTTATTAAACAGGATGATGGAACAGTT
----+----+----+----+----+----+----+----+----+----+----+----+ 4980
CGACCGATGTCATTTTGACGTCCATTGACCCAACAATAATTTGTCCTACTACCTTGTCAA Ala Gly Tyr Ser Lys Thr Ala Gly Asn Trp Val Val Ile Lys Gln Asp Asp Gly Thr Val
                                      Yoml
```

FIG._1K-1

```
GCCAAGTACATGCACATGCTTAACACTCCTTCTGTAAAAGCAGGTCAATCAGTTAAAGCC
     +         +         +         +         +         +         5040
CGGTTCATGTACGTGTACGAATTGTGAGGAAGACATTTCGTCCAGTTAGTCAATTTCGG

Ala Lys Tyr Met His Met Leu Asn Thr Pro Ser Val Lys Ala Gly Gln Ser Val Lys Ala
                                                  YomI

GGTCAAACTATTGGTAAAGTTGGTAGTACAGGGAACTCGACTGGGAACCACCTTCATTTA
     +         +         +         +         +         +         5100
CCAGTTTGATAACCATTTCAACCATCATGTCCCTTGAGCTGACCCTTGGTGGAAGTAAAT

Gly Gln Thr Ile Gly Lys Val Gly Ser Thr Gly Asn Ser Thr Gly Asn His Leu His Leu
                                                         YomI

CAGATCGAACAAAATGGAAAAACAATCGATCCTGAAAAGTACATGCAAGGTATTGGAACT
     +         +         +         +         +         +         5160
GTCTAGCTTGTTTTACCTTTTTGTTAGCTAGGACTTTTCATGTACGTTCCATAACCTTGA

Gln Ile Glu Gln Asn Gly Lys Thr Ile Asp Pro Glu Lys Tyr Met Gln Gly Ile Gly Thr
                                                               YomI

TCTATTTCAGATGCGTCACAAGCTGAGGCAGAACGACAACAAGGGATAGCTCAGGCTAAA
     +         +         +         +         +         +         5220
AGATAAAGTCTACGCAGTGTTCGACTGTTCGACTCCGTCTTGCTGTTGTTCCCTATCGAGTCCGATTT

Ser Ile Ser Asp Ala Ser Gln Ala Glu Ala Glu Arg Gln Gln Gly Ile Ala Gln Ala Lys
                                                              YomI
```

*FIG._1K-2*

```
TCTGATCTTCTCTCCCTCCAAGGAGATATCAGTTCAGTCAATGATCAGATTCAAGAACTT
   ----+----+----+----+----+----+----+----+----+----+----+----+   5280
AGACTAGAGAGAGGGAGGTTCCTCTATAGTCAAGTCAGTTACTAGTCTAAGTTCTTGAA
Ser Asp Leu Leu Ser Leu Gln Gly Asp Ile Ser Ser Val Asn Asp Gln Ile Gln Glu Leu
                                                    Yoml CAGTATGAACTAGTTCAATCTAAAACTCGATGAGTTTGATAAAAGAATTGGAGATTTGAT
   ----+----+----+----+----+----+----+----+----+----+----+----+   5340
GTCATACTTGATCAAGTTAGATTTGAGCTACTCAAACTATTTTCTTAACCTCTAAAACTA
Gln Tyr Glu Leu Val Gln Ser Lys Leu Asp Glu Phe Asp Lys Arg Ile Gly Asp Phe Asp
                                    Yoml GTTCGGGATAGCAAAAGATGAGTCAATGGCTAACAGATACACTTCTGACAGCAAGGAATTC
   ----+----+----+----+----+----+----+----+----+----+----+----+   5400
CAAGCCTATCGTTTTCTACTCAGTTACCGATTGTCTATGTGAAGACTGTCGTTCCTTAAG
Val Arg Ile Ala Lys Asp Glu Ser Met Ala Asn Arg Tyr Thr Ser Asp Ser Lys Glu Phe
                                        Yoml CGAAAATACACCCTCTGATCAGAAAAAAGCTGTGGCAGAGCAAGCTAAAATCCAACAACAA
   ----+----+----+----+----+----+----+----+----+----+----+----+   5460
GCTTTTATGTGGGAGACTAGTCTTTTTTCGACACCGTCTCGTTCGATTTAGGTTGTTGTT
Arg Lys Tyr Thr Ser Asp Gln Lys Lys Ala Val Ala Glu Gln Ala Lys Ile Gln Gln Gln
                                    Yoml
```

FIG. _1L-1

```
AAAGTTAATTGGATTCAAAAAGAAATTAAAACAAATAAAGCATTGAACTCCGCTCAACGT
     ----+----+----+----+----+----+----+----+----+----+----+----+  5520
TTTCAATTAACCTAAGTTTTTCTTTAATTTTGTTTATTCGTAACTTGAGGCGAGTTGCA

Lys Val Asn Trp Ile Gln Lys Glu Ile Lys Thr Asn Lys Ala Leu Asn Ser Ala Gln Arg
    └─Yoml─────────────────────────────────────────────────────────────────

GCACAGCTTCAAGAAGAGCTTAAACAGGCCAAGCTAGATTAATTTCTGTTCAAGACCAG
     ----+----+----+----+----+----+----+----+----+----+----+----+  5580
CGTGTCGAAGTTCTTCTCGAATTTGTCCGGTTCGATCTAATTAAAGACAAGTTCTGGTC

Ala Gln Leu Gln Glu Glu Leu Lys Gln Ala Lys Leu Asp Leu Ile Ser Val Gln Asp Gln
    └─Yoml─────────────────────────────────────────────────────────────────

GTTCGTGAGCTACAGAAACAACTTGTTCAATCTAAAGTTGATGAGACACTTAAGTCAATT
     ----+----+----+----+----+----+----+----+----+----+----+----+  5640
CAAGCACTCGATGTCTTTGTTGAACAAGTTAGATTTCAACTACTCTGTGAATTCAGTTAA

Val Arg Glu Leu Gln Lys Gln Leu Val Gln Ser Lys Val Asp Glu Thr Leu Lys Ser Ile
    └─Yoml─────────────────────────────────────────────────────────────────

GAAAAGTCATCTTCTAAAACCCAAGGGAAAATTAAAGATGTCGATAACAAAATTCAATG
     ----+----+----+----+----+----+----+----+----+----+----+----+  5700
CTTTTCAGTAGAAGATTTTGGGTTCCCTTTTAATTTCTACAGCTATTGTTTAAGTTAC

Glu Lys Ser Ser Lys Thr Gln Gly Lys Ile Lys Asp Val Asp Asn Lys Ile Ser Met
    └─Yoml─────────────────────────────────────────────────────────────
```

FIG._1L-2

```
ACTGAAGAAGATGAAGACAAGGTTAAATACTATAGCAAGCAAATAAAGCTCATTCAACAA
----+----+----+----+----+----+----+----+----+----+----+----+  5760
TGACTTCTTCTACTTCTGTTCCAATTTATGATATCGTTCGTTATTTCGAGTAAGTTGTT
Thr Glu Glu Asp Lys Val Lys Tyr Tyr Ser Lys Gln Ile Lys Leu Ile Gln Gln
                                            YomI

CAACAAAAGGAAGCGAAGAAATACATTAAGCAGCTTGAAGAACAAAAGAAAGCTGCGAAA
----+----+----+----+----+----+----+----+----+----+----+----+  5820
GTTGTTTTCCTTCGCTTCTTTATGTAATTCGTCGAACTTCTTGTTTTCTTTCGACGCTTT
Gln Gln Lys Glu Ala Lys Lys Tyr Ile Lys Gln Leu Glu Gln Lys Lys Ala Ala Lys
                                         YomI

GGTTCCCTGACATCCAGGAACAGAGATCACTGAAGAAATGCAAAACTGGAAAGATAAACAG
----+----+----+----+----+----+----+----+----+----+----+----+  5880
CCAAAGGGACTGTAGGTCCTTGTCTCTAGTGACTTCTTTACGTTTTGACCTTTCTATTTGTC
Gly Phe Pro Asp Ile Gln Glu Gln Ile Thr Glu Glu Met Gln Asn Trp Lys Asp Lys Gln
                                         YomI

AAAGATTTTAACCTTGAGCTTTATAACACCAAGAAGTCGATCAAGGATATCTATAAATCA
----+----+----+----+----+----+----+----+----+----+----+----+  5940
TTTCTAAAATTGGAACTCGAAATATTGTGGTTCTTCAGCTAGTTCCTAGTAGATATTTAGT
Lys Asp Phe Asn Leu Glu Leu Tyr Asn Thr Lys Lys Ser Ile Lys Asp Ile Tyr Lys Ser
                                         YomI
```

FIG._1M-1

```
TTGGCTGATGAAGTTGTATCCATCTACAAAGAGATGTACGAAAAATGCCTGATATTGAG
     ----+----+----+----+----+----+----+----+----+----+----+----+  6000
AACCGACTACTTCAACATAGGTAGATGTTTCTCTACATGCTTTTTACGCCACTATAACTC

Leu Ala Asp Glu Val Val Ser Ile Tyr Lys Glu Met Tyr Glu Lys Met Arg Asp Ile Glu
                                    YomI

TTAGAAGCGCATCAGAAAGGCGACTCAAGACTTGATCGATGAGATAGACAAGACTGATGAC
     ----+----+----+----+----+----+----+----+----+----+----+----+  6060
AATCTTCGCGTAGTCTTTCCGCTGAGTTCTGAACTAGCTACTCTATCTGTTCTGACTACTG

Leu Glu Ala His Gln Lys Ala Thr Gln Asp Leu Ile Asp Glu Ile Asp Lys Thr Asp Asp
                                    YomI

GAGGCTAAATTTCAAAAGAATTAAAAGAAGACAAGACAGTATTCAAAAGTTGACTGAC
     ----+----+----+----+----+----+----+----+----+----+----+----+  6120
CTCCGATTTAAAGTTTTCTTAATTTTCTTCTGTTCTGTCATAAGTTTTCAACTGACTG

Glu Ala Lys Phe Gln Lys Glu Leu Lys Glu Arg Gln Asp Ser Ile Gln Lys Leu Thr Asp
                                    YomI

CAAATTAATCAATACTCTCTTGATGATTCGAATTCGGAAAGTCAAAGTCAAAGAACTA
     ----+----+----+----+----+----+----+----+----+----+----+----+  6180
GTTTAATTAGTTATGAGAGAACTACTAAGACTTAAGCCTTTCAGTTTTCAGTTTCTTGAT

Gln Ile Asn Gln Tyr Ser Leu Asp Asp Ser Glu Phe Gly Lys Ser Lys Val Lys Glu Leu
                                    YomI
```

*FIG._1M-2*

```
ACTGAACAGCTTCAAAAGAGCAGTTAGACCTTGATGATTTTCTAAAGGATCGCGAAAGT
     ----+----|----+----|----+----|----+----|----+----|----+----|  6240
TGACTTGTCGAAGTTTTCTCGTCAATCTGGAACTACTAAAAGATTTCCTAGCGCTTTCA
Thr Glu Gln Leu Gln Lys Glu Gln Leu Asp Asp Phe Leu Lys Asp Arg Glu Ser
                                                    Yoml AACAAACGGAAAAGAAGGCGCTCCAAGATCAGCTCGAAAAAGATGAGGAGTCAATCAACAAT
     ----+----|----+----|----+----|----+----|----+----|----+----|  6300
TTGTTTGCCTTTTCTTCCGCGAGGTTCTAGTCGAGCTTTTTCTACTCCTCAGTTAGTTGTTA
Asn Lys Arg Lys Glu Ala Leu Gln Asp Gln Leu Glu Lys Asp Glu Ser  Ile  Asn Asn
                                                    Yoml AAATACGATAATCTTGTAAATGATGAACGAGCCTTTAAAAAGCTTGAGGATAAGATTATG
     ----+----|----+----|----+----|----+----|----+----|----+----|  6360
TTTATGCTATTAGAACATTTACTACTTGCTCGGAAATTTTCGAACTCCTATTCTAATAC
Lys Tyr Asp Asn Leu Val Asn Asp Glu Arg Ala Phe Lys Lys Leu Glu Asp Lys Ile Met
                                                    Yoml AATGGAAAAATCACCGATATCGCTAAGCAGCTTAATGAGTTTTCTAAGTTTATTAATACC
     ----+----|----+----|----+----|----+----|----+----|----+----|  6420
TTACCTTTTTAGTGGCTATAGCGATTCGTCGAATTACTCAAAAGATTCAAATAATTATGG
Asn Gly Lys Ile Thr Asp Ile Ala Lys Gln Leu Asn Glu Phe Ser Lys Phe Ile Asn Thr
                                                    Yoml
```

FIG._1N-1

```
AATATGGAGTCCATTGGAAAAAGTATTTCAAACAACCTGATTGATAAACTCAAAGAAGCA
    |----+----|----+----|----+----|----+----|----+----|----+----|  6480
TTATACCTCAGGTAACCTTTTTCATAAAGTTTGTTGGACTAACTATTTGAGTTTCTTCGT

Asn Met Glu Ser Ile Gly Lys Ser Ile Ser Asn Asn Leu Ile Asp Lys Leu Lys Glu Ala
                              Yoml
```

```
TCTAATGCACTGAATACGCTGTCTCAAAGGCAACACGACAGGTAAAAAAGTATCCTCTTTC
    |----+----|----+----|----+----|----+----|----+----|----+----|  6540
AGATTACGTGACTTATGACGACAGTTTCCGTTGTGCTGTCCATTTTTTCATAGGAGAAAG

Ser Asn Ala Leu Asn Thr Ala Val Lys Gly Asn Thr Thr Gly Lys Lys Val Ser Ser Phe
                              Yoml
```

```
GCTTCTGGAGGGTACACACTGGAACAGGATTAGGTGCTGGTAAACTTGCATTCCTACATGAC
    |----+----|----+----|----+----|----+----|----+----|----+----|  6600
CGAAGACCTCCCATGTGACCTTGTCCTAATCCACGACCATTGAACGTAAGGATGTACTG

Ala Ser Gly Gly Tyr Thr Gly Leu Gly Ala Gly Lys Leu Ala Phe Leu His Asp
                              Yoml
```

```
AAAGAACTGATCTTAAATAAAACTGACACAGCCAACATCCTTGATACGGTAAAAGCTGTT
    |----+----|----+----|----+----|----+----|----+----|----+----|  6660
TTTCTTGACTAGAATTTATTTTGACTGTGTCGGTTGTAGGAACTATGCCATTTTCGACAA

Lys Glu Leu Ile Leu Asn Lys Thr Asp Thr Ala Asn Ile Leu Asp Thr Val Lys Ala Val
                              Yoml
```

FIG._1N-2

```
CGTGAAACCGCTGTGTGGACGATTCCCCAAAATGGGGCCAAGGAGTAAAATTAGCAGACCTT
----------+---------+---------+---------+---------+---------+  6720
GCACTTTGGCGACACCTGCTAAGGGGTTTACCCGGTTCCTCATTTAATCGTCTGGAA

Arg Glu Thr Ala Val Asp Asp Ser Pro Lys Trp Gly Gln Gly Val Lys Leu Ala Asp Leu
                                          Yoml ATTAAAAAGGAATTACTTCTATTCCTTCATTAGTTCCTAACGTTAATCAATCAATGTTA
----------+---------+---------+---------+---------+---------+  6780
TAATTTTTCCTTAATGAAGATAAGGAAGTAATCAAGGATTGCAATTAGTTAGTTACAAT Ile Lys Lys Gly Ile Thr Ser Ile Pro Ser Leu Val Pro Asn Val Asn Gln Ser Met Leu
                                          Yoml ACAAACAGTTTAATTCCAAAATTTAAAGAAGATTGAGATCCCCTCAAAAACAATTGCTTCT
----------+---------+---------+---------+---------+---------+  6840
TGTTTGTCAAATTAAGGTTTAAATTTCTTCTAACTCTAGGGGAGTTTTTGTTAACGAAGA Thr Asn Ser Leu Ile Pro Asn Leu Lys Lys Ile Glu Ile Pro Ser Lys Thr Ile Ala Ser
                                          Yoml TCTGGAGATAAAACAATTAATTAACGAATACTTTCCACATTGATAAGCTAATAGGAGGA
----------+---------+---------+---------+---------+---------+  6900
AGACCCTCTATTTTGTTAATTAATTGCTTATGAAAGGTGTAACTATTCGATTATCCTCCT Ser Gly Asp Lys Thr Ile Asn Leu Thr Asn Thr Phe His Ile Asp Lys Leu Ile Gly Gly
                                          Yoml
```

FIG._10-1

```
GAATCGGGAGCGAGATCGATGTTTGAAAGCATTAAAAACGAAGTTGTAAAACTAAATGGT
     ----+----|----+----|----+----|----+----|----+----|----+----|   6960
CTTAGCCCTCGCTCTAGCTACAAACTTTCGTAATTTTGCTTCAACATTTTGATTTACCA

Glu Ser Gly Ala Arg Ser Met Phe Glu Ser Ile Lys Asn Glu Val Val Lys Leu Asn Gly
                                    ─Yoml─────────────────────────────────

AGCATGTAAGAGTCTGCAAAAGCAGAGACTCTTTATTTAACTTAACTTGAGGTGGAAACTCA
     ----+----|----+----|----+----|----+----|----+----|----+----|   7020
TCGTACATTCTCAGACGTTTCGTCTCTGAGAAATAAATTGAATTGAACTCCACCTTTGAGT

Ser Met
─Yoml─┘

TGATTAGAGAAAGTCAATACTTTATGTTCAATAATATCCCTTCTTATGAATTAGGAGCCG
     ----+----|----+----|----+----|----+----|----+----|----+----|   7080
ACTAATCTCTTTCAGTTATGAAATACAAGTTATTATAGGGAAGAATACTTAATCCTCGGC

TAAATGTAAATACAGAAGGA
     ----+----|----+──▶   7100
ATTTACATTTATGTCTTCCT
```

FIG._10-2

```
lasa_psea.pe    PKVLLTLMVMQSGPLGAPDERALAAPLGRLSAKRGFD-AQVRDVLQQLSRRYYGFEEYQL
                         :: | : | : | :  |:|| |  ||:
YOMI            IVTSTTSSGGTPSSTGGSYSGKYSSYINSAASKYNVDPALIAAVIQQES----GFN---
                1400      1410      1420      1430      1440      1450 lasa_psea.pe    RQAAARKAVGEDGLNA---ASAALLGLLREGAKVSAVQGGNPLGAYAQTFQRLFGTPAAE
                  | ::: |  ||  :    | ::|| ||  ::|| ||   ||  |:  | :  :
YOMI            --AKARSGVGAMGLMQLMPATAKSLGVNNAYDPYQNVMGGTKY--LAQQLEK-FGGNVEK
                  1460      1470      1480      1490      1500 lasa_psea.pe    LLQPSNRVARQLQAKAALAPPSNLMQLPWRQ---GYSWQPNGAHSNTGSGYPYSS-FDAS
                 ::  |: ||  | ||   ::  |  | :    | ::|   :|   ::  |  :  : |
YOMI            ALAAYNAGPGNV-IKYGGIPPFKETQNYVKKIMANYSKSLSSATSSIASYYTNNSAFRVS
                1510      1520      1530      1540      1550      1560 lasa_psea.pe    YDWPRWGSATYSV------VAAHAGT-VRVLSRCQVRVTHPSGWATNYY--HMDQIQVSN
                  : :: |       |    |:|||   |  : |: ||::: |   | | :|    |::| |:
YOMI            SKYGQQESGLRSSPHKGTDFAAKAGTAIKSLQSGKVQIAGYSKTAGNWVVIKQDDGTVAK
                1570      1580      1590      1600      1610      1620 lasa_psea.pe    GQQV--SADTKLG---VYAGNINTALCEGGSSTGPHLHFSLLYNGAFVSLQGASFGPYRIN
                ::: : ::: | |||:   ::: | |||||:::: | :  :| | |:
YOMI            YMHMLNTPSVKAGQSVKAGQTIGKVGSTGNSTGNHLHLQIEQNGKTIDPE-----KYMQG
                1630      1640      1650      1660      1670      1680 lasa_psea.pe    VGTSNYDNDCRRYYFYNQSAGTTHCAFRPLYNPGLAL
                :|||  |  |
YOMI            IGTSISDASQAEAERQQGIAQAKSDLLSLQGDISSVNDQIQELQYELVQSKLDEFDKRIG
                1690      1700      1710      1720      1730      1740
```

FIG._2

SEQUENCE LISTING

<160> NUMBER OF SEQ ID NOS: 3

<210> SEQ ID NO 1
<211> LENGTH: 7100
<212> TYPE: DNA
<213> ORGANISM: Bacillius subtilis

<400> SEQUENCE: 1

| | | | | | |
|---|---|---|---|---|---|
| atattggcat | ggtgttatgg | atgtaattat | taagaaagca | aacaaagtcg | ctcaataact | 60 |
| gagtggcttt | tttctttgtc | ctctcccta | ctgaaaggaa | gtgattctta | cttgagtcaa | 120 |
| aacctcaaaa | ttatactaac | cccgcaagct | gatacctcat | ccaaaactgt | cgaacagtta | 180 |
| aatcagcaaa | ttaaatccct | ggaaaagaaa | ctcaactccc | tcaagctcaa | tacaaacatt | 240 |
| gattctacaa | ccttaaaagc | tctgcaagaa | ttctcctctg | ctatcgacac | atatcagaaa | 300 |
| aacctaaaat | cctataatca | aacagttaaa | gaaacctcaa | cagtaattaa | gaatgctgac | 360 |
| ggatcagttg | aaaagctcac | ccagcagtat | aagaaaaatg | gtgagatact | tcaacgtgaa | 420 |
| acaaaaataa | tcaacaatcg | taatacagca | ttaaagcaag | aaactcaaga | ggttaacaag | 480 |
| ctaacacagg | ccactgagaa | actaggacag | gttcaaaaaa | agactgtgca | gagaaatctg | 540 |
| caaggacagc | caacaaaggt | agtgcagaaa | aaccgccacg | ggttcgatga | tattgtttat | 600 |
| acaactgatc | ctaaaactaa | ttcgacctcc | tcaaaaacta | caactaatta | tgaccaacaa | 660 |
| aggagagcaa | ttgagcagct | taagcaagat | ttagagaagc | ttagacagca | aggtattgtt | 720 |
| actgatacga | ccatctcatc | tcttggccga | aaaataaaca | cagctcaatc | cgctcaacaa | 780 |
| attgaagcac | tgcaaaatag | gataaggatg | ttagatgata | aatctgcggc | agttgcgaag | 840 |

-continued

```
aacaatgaat taaagaaaac cattgaatta tatcagcgac aggcacaagt aaatgttcaa    900
aacctaaata cacggtatgg cagttctatg ggctctagta atagacaagc tgttcaagat    960
tatttgaatg cagtaaatag tcttaatgta agcactggaa gcaataatat cagatcacaa   1020
attcaaagct tgaatatgca atttagagaa ttagcctcca acgctcaaac agctgctaat   1080
caagcctctt cttttggagc agaactaacc caaaccttca aaagcatgtc cacctattta   1140
atctccggtt ctttattcta cggagctatc tctggactta agaaatggt atcccaggca    1200 atagaaattg atactctcat gacaaatatt cgccgtgtta tgaatgagcc ggattataaa   1260
tataatgaac ttctccaaga atctattgac ttaggtgata cactttcaaa taaaatcaca   1320
gatattcttc aaatgacagg cgattttggg agaatggggtt tcgatgaaag tgagctctcc  1380
acgttaacga aaactgccca agttcttcaa aatgtctctg atttaactcc cgatgataca   1440
gttaacactc taacgcagc aatgctcaac tttaatattg cagcaaatga ttcaatatca    1500
attgcagata aattaaatga ggttgataat aactatgctg ttacaactct agatctggcc   1560
aattctatcc gtaaagctgg ttcaactgct tctacattcg gggtagagct aaatgatctt   1620
attggttata caactgcaat tgctagtaca acacgtgaat cagggaatat cgtcgggaac   1680
tccttaaaga caattttcgc gcggattggg aataatcaaa gctcaattaa agcgttagaa   1740
cagattggta tctcagttaa aacagctggt ggtgaagcta atcagcaag tgatttaatt    1800 agtgaagttg ctggtaagtg ggatacgctt tctgatgctc agaaacaaaa tacttcaatt   1860
ggagtagctg gtatttatca attatcccgt tttaatgcaa tgatgaacaa cttctctatt   1920
gctcagaatg cggctaaaac tgcggctaac tcaacaggaa gtgcttggag tgagcagcaa   1980
aagtatgcag atagtctaca agctagggta aataagcttc aaaataactt cactgaattt   2040
gctattgcag cttctgatgc ttttattagc gacggattaa ttgaatttac tcaagccgca   2100
ggttctttgc ttaacgcttc tacaggagta atcaaatcag ttgggttcct acctcccctt   2160
ttagctgcag taagcactgc aacccttttg ctcagtaaga ataccgcac attagccagc    2220 agcctaattt tgggcacacg tgcaatgggg caagaaactt tagcgactgc tgggctagaa   2280
gctggtatga ctcgtgcagc agtcgcctca agagttctaa aaactgctct tcgagggttg   2340
cttgtttcaa ctttagttgg cggtgcattt gctgctttgg gatgggcgct agaatcatta   2400
atttcttctt ttgcagaagc taaaaaagct aaagatgatt ttgagcagag ccagcaaacc   2460
aatgtcgaag caattacgac caataaagac tccactgata aactaataca gcaatataaa   2520
gagcttcaaa aagttaaaga gtcaagatct ttaacttcag atgaagagca agaataccttt  2580 caagtcactc agcaattagc acaaactttc cctgcattag ttaaaggcta tgattctcaa   2640
ggaaatgcaa ttcttaagac aaataaagag cttgaaaaag cgattgagaa tactaaagag   2700
tatttggctt taaagaaaca agaaacaaga gacagcgcaa agaaaacatt cgaagacgct   2760
tctaaggaaa ttaaaaagtc taaggatgaa ttaaagcagt acaaacaaat agctgactac   2820
aacgataaag gtagacctaa atgggatctc attgcagatg acgatgacta taaggttgca   2880
gctgataaag ctaaacaaag tatgctcaaa gctcaatctg acattgagag tggaaatgct   2940
aaagttaaag atagcgtcct ttcaattgca aatgcttata gttcaattga tatcagtaat   3000
actttaaaga cgagtattag tgatgttgtc aacaaactta acttaaaaga tgatttagat   3060
cctgaagaat tagaaaaatt ctcctcttct ttaggaaagc ttcaagaaaa aatgcaaaaa   3120
gctttagatt caggcgatga aaaagctttc gataacgcaa aaaaagatct tcaaagtctc   3180
```

```
ttggaaacat actccaaatc cgattcttct attgatgttt ttaaaatgag cttcgacaaa    3240
gcacagaaga acataaaaga tggagataag agcttatctt ccgtcaaatc tgaagttggt    3300
gatttaggtg agacgctggc agaagcaggt aacgaggcag aagattttgg taagaagcta    3360
aaagaagctc tggatgcaaa tagtgttgat gatattaagg cagctattaa agaaatgtca    3420
gatgctatgc agttcgattc cgttcaagat gtcttaaatg gggatatttt taataacacc    3480
aaagatcaag tagctcctct caatgatctt ctggaaaaaa tggctgaagg taaaagtatt    3540
tctgcaaatg aagctaatac ccttattcaa aaagataagg aacttgccca ggctattagc    3600
atcgaaaatg gcgttgtgaa aattaaccgt gatgaagtta tcaaacaaag aaaagttaaa    3660
cttgatgctt ataacgacat ggttacctac agcaataaat tgatgaaaac agaagttaac    3720
aacgctatca aaactttaaa cgctgatacc ttacggattg acagcctgaa aaagctacga    3780
aaagaacgaa agcttgatat gtctgaggcc gaactgtcag acctagaagt taagtcaatt    3840
aataatgttg cagatgcaaa aaagaactt aaaaagcttg aagagaaaat gcttcaacct    3900
ggtggatact ccaatagtca aattgaagca atgcaaagcg ttaaatcagc tttagaatct    3960
tatatttctg catctgaaga agccaccagt acacaagaaa tgaataaaca ggcacttgtt    4020
gaagctggaa catcattgga gaattggaca gatcaacaag aaaaagccaa tgaagaaacc    4080
aagacttcca tgtatgttgt tgataaatac aaggaagcat tagaaaaagt taatgctgag    4140
attgacaagt acaacaagca ggtcaatgat tatcctaaat actctcagaa atatcgagat    4200
gcaatcaaga aagaaattaa agcacttcag caaaagaaaa agcttatgca ggaacaagct    4260
aagctgctta agatcaaat taaatccggt aacattactc aatacggtat tgtaacctct    4320
acaacttctt ctggtggaac cccctcctca actggtggat catattcagg caagtattca    4380
agctacataa attcagcagc tagtaaatac aatgttgacc ctgcccttat tgcagctgta    4440
attcagcaag aatcagggtt taatgctaaa gcacgatctg gtgtaggtgc catgggatta    4500
atgcaactga tgccagcaac agcaaaaagc ttaggagtaa ataacgctta cgatccttat    4560
caaaatgtta tgggtggaac aaagtacctc gcccaacaac ttgaaaagtt tggcggtaat    4620
gttgaaaaag cattggctgc atataatgct gggcctggta acgtaattaa atatggtggt    4680
atccctcctt ttaaagaaac acagaattac gtcaagaaga tcatggccaa ctatagcaaa    4740
tcgctctcat ctgccacttc ttcaatcgcc agctattata caaataatag cgcttttagg    4800
gtaagctcca aatatggaca acaggaatct ggtctccgct cctccccaca caaaggaact    4860
gattttgctg caaaagcagg tacagcaatt aaatctcttc aaagtggtaa agtccaaatt    4920
gctggctaca gtaaaactgc aggtaactgg gttgttatta acaggatga tggaacagtt    4980 gccaagtaca tgcacatgct taacactcct tctgtaaaag caggtcaatc agttaaagcc    5040
ggtcaaacta ttggtaaagt tggtagtaca gggaactcga ctgggaacca ccttcattta    5100
cagatcgaac aaaatggaaa aacaatcgat cctgaaaagt acatgcaagg tattggaact    5160
tctatttcag atgcgtcaca agctgaggca gaacgacaac aagggatagc tcaggctaaa    5220
tctgatcttc tctccctcca aggagatatc agttcagtca atgatcagat tcaagaactt    5280
cagtatgaac tagttcaatc taaactcgat gagtttgata aagaattgg agattttgat    5340 gttcggatag caaagatga gtcaatggct aacagataca cttctgacag caaggaattc    5400
cgaaaataca cctctgatca gaaaaaagct gtggcagagc aagctaaaat ccaacaacaa    5460
aaagttaatt ggattcaaaa agaaattaaa acaaataaag cattgaactc cgctcaacgt    5520
gcacagcttc aagaagagct taaacaggcc aagctagatt taatttctgt tcaagaccag    5580
```

-continued

```
gttcgtgagc tacagaaaca acttgttcaa tctaaagttg atgagacact taagtcaatt    5640
gaaaagtcat cttctaaaac ccaagggaaa attaaagatg tcgataacaa aatttcaatg    5700
actgaagaag atgaagacaa ggttaaatac tatagcaagc aaataaagct cattcaacaa    5760
caacaaaagg aagcgaagaa atacattaag cagcttgaag aacaaagaa agctgcgaaa     5820 ggtttccctg acatccagga acagatcact gaagaaatgc aaaactggaa agataaacag    5880
aaagatttta accttgagct ttataacacc aagaagtcga tcaaggatat ctataaatca    5940
ttggctgatg aagttgtatc catctacaaa gagatgtacg aaaaaatgcg tgatattgag    6000
ttagaagcgc atcagaaagc gactcaagac ttgatcgatg agatagacaa gactgatgac    6060
gaggctaaat ttcaaaaaga attaaaagaa agacaagaca gtattcaaaa gttgactgac    6120
caaattaatc aatactctct tgatgattct gaattcggaa agtcaaaagt caagaactta    6180
actgaacagc ttcaaaaaga gcagttagac cttgatgatt ttctaaagga tcgcgaaagt    6240
aacaaacgga agaagcgct ccaagatcag ctcgaaaaag atgaggagtc aatcaacaat    6300
aaatacgata tcttgtaaa tgatgaacga gcctttaaaa agcttgagga taagattatg    6360
aatggaaaaa tcaccgatat cgctaagcag cttaatgagt tttctaagtt tattaatacc    6420
aatatggagt ccattggaaa aagtatttca acaacctga ttgataaact caaagaagca    6480
tctaatgcac tgaatactgc tgtcaaaggc aacacgacag gtaaaaaagt atcctctttc    6540
gcttctggag ggtacactgg aacaggatta ggtgctggta aacttgcatt cctacatgac    6600
aaagaactga tcttaaataa aactgacaca gccaacatcc ttgatacggt aaaagctgtt    6660
cgtgaaaccg ctgtggacga ttccccaaaa tggggccaag gagtaaaatt agcagacctt    6720
attaaaaaag gaattacttc tattccttca ttagttccta acgttaatca atcaatgtta    6780
acaaacagtt taattccaaa tttaaagaag attgagatcc cctcaaaaac aattgcttct    6840
tctggagata aaacaattaa tttaacgaat actttccaca ttgataagct aataggagga    6900
gaatcgggag cgagatcgat gtttgaaagc attaaaaacg aagttgtaaa actaaatggt    6960
agcatgtaag agtctgcaaa agcagactct ttatttaact taacttgagg tggaaactca    7020
tgattagaga aagtcaatac tttatgttca ataatatccc ttcttatgaa ttaggagccg    7080
taaatgtaaa tacagaagga                                                7100
```

<210> SEQ ID NO 2
<211> LENGTH: 2285
<212> TYPE: PRT
<213> ORGANISM: Bacillius subtilis

<400> SEQUENCE: 2

```
Leu Ser Gln Asn Leu Lys Ile Ile Leu Thr Pro Gln Ala Asp Thr Ser
  1               5                  10                  15

Ser Lys Thr Val Glu Gln Leu Asn Gln Gln Ile Lys Ser Leu Glu Lys
             20                  25                  30

Lys Leu Asn Ser Leu Lys Leu Asn Thr Asn Ile Asp Ser Thr Thr Leu
         35                  40                  45

Lys Ala Leu Gln Glu Phe Ser Ser Ala Ile Asp Thr Tyr Gln Lys Asn
     50                  55                  60

Leu Lys Ser Tyr Asn Gln Thr Val Lys Glu Thr Ser Thr Val Ile Lys
 65                  70                  75                  80

Asn Ala Asp Gly Ser Val Glu Lys Leu Thr Gln Gln Tyr Lys Lys Asn
             85                  90                  95
```

-continued

```
Gly Glu Ile Leu Gln Arg Glu Thr Lys Ile Ile Asn Asn Arg Asn Thr
                100                 105                 110

Ala Leu Lys Gln Glu Thr Gln Glu Val Asn Lys Leu Thr Gln Ala Thr
            115                 120                 125

Glu Lys Leu Gly Gln Val Gln Lys Lys Thr Val Gln Arg Asn Leu Gln
        130                 135                 140

Gly Gln Pro Thr Lys Val Val Gln Lys Asn Arg His Gly Phe Asp Asp
145                 150                 155                 160

Ile Val Tyr Thr Thr Asp Pro Lys Thr Asn Ser Thr Ser Ser Lys Thr
                165                 170                 175

Thr Thr Asn Tyr Asp Gln Gln Arg Arg Ala Ile Glu Gln Leu Lys Gln
            180                 185                 190

Asp Leu Glu Lys Leu Arg Gln Gln Gly Ile Val Thr Asp Thr Thr Ile
        195                 200                 205

Ser Ser Leu Gly Arg Lys Ile Asn Thr Ala Gln Ser Ala Gln Gln Ile
    210                 215                 220

Glu Ala Leu Gln Asn Arg Ile Arg Met Leu Asp Asp Lys Ser Ala Ala
225                 230                 235                 240

Val Ala Lys Asn Asn Glu Leu Lys Lys Thr Ile Glu Leu Tyr Gln Arg
                245                 250                 255

Gln Ala Gln Val Asn Val Gln Asn Leu Asn Thr Arg Tyr Gly Ser Ser
            260                 265                 270

Met Gly Ser Ser Asn Arg Gln Ala Val Gln Asp Tyr Leu Asn Ala Val
        275                 280                 285

Asn Ser Leu Asn Val Ser Thr Gly Ser Asn Asn Ile Arg Ser Gln Ile
    290                 295                 300

Gln Ser Leu Asn Met Gln Phe Arg Glu Leu Ala Ser Asn Ala Gln Thr
305                 310                 315                 320

Ala Ala Asn Gln Ala Ser Ser Phe Gly Ala Glu Leu Thr Gln Thr Phe
                325                 330                 335

Lys Ser Met Ser Thr Tyr Leu Ile Ser Gly Ser Leu Phe Tyr Gly Ala
            340                 345                 350

Ile Ser Gly Leu Lys Glu Met Val Ser Gln Ala Ile Glu Ile Asp Thr
        355                 360                 365

Leu Met Thr Asn Ile Arg Arg Val Met Asn Glu Pro Asp Tyr Lys Tyr
    370                 375                 380

Asn Glu Leu Leu Gln Glu Ser Ile Asp Leu Gly Asp Thr Leu Ser Asn
385                 390                 395                 400

Lys Ile Thr Asp Ile Leu Gln Met Thr Gly Asp Phe Gly Arg Met Gly
                405                 410                 415

Phe Asp Glu Ser Glu Leu Ser Thr Leu Thr Lys Thr Ala Gln Val Leu
            420                 425                 430

Gln Asn Val Ser Asp Leu Thr Pro Asp Asp Thr Val Asn Thr Leu Thr
        435                 440                 445

Ala Ala Met Leu Asn Phe Asn Ile Ala Ala Asn Asp Ser Ile Ser Ile
    450                 455                 460

Ala Asp Lys Leu Asn Glu Val Asp Asn Asn Tyr Ala Val Thr Thr Leu
465                 470                 475                 480

Asp Leu Ala Asn Ser Ile Arg Lys Ala Gly Ser Thr Ala Ser Thr Phe
                485                 490                 495

Gly Val Glu Leu Asn Asp Leu Ile Gly Tyr Thr Thr Ala Ile Ala Ser
            500                 505                 510

Thr Thr Arg Glu Ser Gly Asn Ile Val Gly Asn Ser Leu Lys Thr Ile
```

-continued

```
                515                 520                 525
Phe Ala Arg Ile Gly Asn Asn Gln Ser Ser Ile Lys Ala Leu Glu Gln
        530                 535                 540
Ile Gly Ile Ser Val Lys Thr Ala Gly Gly Glu Ala Lys Ser Ala Ser
545                 550                 555                 560
Asp Leu Ile Ser Glu Val Ala Gly Lys Trp Asp Thr Leu Ser Asp Ala
                565                 570                 575
Gln Lys Gln Asn Thr Ser Ile Gly Val Ala Gly Ile Tyr Gln Leu Ser
                580                 585                 590
Arg Phe Asn Ala Met Met Asn Asn Phe Ser Ile Ala Gln Asn Ala Ala
        595                 600                 605
Lys Thr Ala Ala Asn Ser Thr Gly Ser Ala Trp Ser Glu Gln Gln Lys
        610                 615                 620
Tyr Ala Asp Ser Leu Gln Ala Arg Val Asn Lys Leu Gln Asn Asn Phe
625                 630                 635                 640
Thr Glu Phe Ala Ile Ala Ala Ser Asp Ala Phe Ile Ser Asp Gly Leu
                645                 650                 655
Ile Glu Phe Thr Gln Ala Ala Gly Ser Leu Leu Asn Ala Ser Thr Gly
                660                 665                 670
Val Ile Lys Ser Val Gly Phe Leu Pro Pro Leu Leu Ala Ala Val Ser
        675                 680                 685
Thr Ala Thr Leu Leu Leu Ser Lys Asn Thr Arg Thr Leu Ala Ser Ser
        690                 695                 700
Leu Ile Leu Gly Thr Arg Ala Met Gly Gln Glu Thr Leu Ala Thr Ala
705                 710                 715                 720
Gly Leu Glu Ala Gly Met Thr Arg Ala Ala Val Ala Ser Arg Val Leu
                725                 730                 735
Lys Thr Ala Leu Arg Gly Leu Leu Val Ser Thr Leu Val Gly Gly Ala
                740                 745                 750
Phe Ala Ala Leu Gly Trp Ala Leu Glu Ser Leu Ile Ser Ser Phe Ala
        755                 760                 765
Glu Ala Lys Lys Ala Lys Asp Asp Phe Glu Gln Ser Gln Gln Thr Asn
        770                 775                 780
Val Glu Ala Ile Thr Thr Asn Lys Asp Ser Thr Asp Lys Leu Ile Gln
785                 790                 795                 800
Gln Tyr Lys Glu Leu Gln Lys Val Lys Glu Ser Arg Ser Leu Thr Ser
                805                 810                 815
Asp Glu Glu Gln Glu Tyr Leu Gln Val Thr Gln Leu Ala Gln Thr
                820                 825                 830
Phe Pro Ala Leu Val Lys Gly Tyr Asp Ser Gln Gly Asn Ala Ile Leu
        835                 840                 845
Lys Thr Asn Lys Glu Leu Glu Lys Ala Ile Glu Asn Thr Lys Glu Tyr
        850                 855                 860
Leu Ala Leu Lys Lys Gln Thr Arg Asp Ser Ala Lys Lys Thr Phe
865                 870                 875                 880
Glu Asp Ala Ser Lys Glu Ile Lys Lys Ser Lys Asp Glu Leu Lys Gln
                885                 890                 895
Tyr Lys Gln Ile Ala Asp Tyr Asn Asp Lys Gly Arg Pro Lys Trp Asp
                900                 905                 910
Leu Ile Ala Asp Asp Asp Asp Tyr Lys Val Ala Ala Asp Lys Ala Lys
        915                 920                 925
Gln Ser Met Leu Lys Ala Gln Ser Asp Ile Glu Ser Gly Asn Ala Lys
        930                 935                 940
```

```
Val Lys Asp Ser Val Leu Ser Ile Ala Asn Ala Tyr Ser Ser Ile Asp
945                 950                 955                 960

Ile Ser Asn Thr Leu Lys Thr Ser Ile Ser Asp Val Val Asn Lys Leu
                965                 970                 975

Asn Leu Lys Asp Asp Leu Asp Pro Glu Glu Leu Glu Lys Phe Ser Ser
            980                 985                 990

Ser Leu Gly Lys Leu Gln Glu Lys Met Gln Lys Ala Leu Asp Ser Gly
        995                 1000                1005

Asp Glu Lys Ala Phe Asp Asn Ala Lys Lys Asp Leu Gln Ser Leu Leu
    1010                1015                1020

Glu Thr Tyr Ser Lys Ser Asp Ser Ser Ile Asp Val Phe Lys Met Ser
1025                1030                1035                1040

Phe Asp Lys Ala Gln Lys Asn Ile Lys Asp Gly Asp Lys Ser Leu Ser
                1045                1050                1055

Ser Val Lys Ser Glu Val Gly Asp Leu Gly Glu Thr Leu Ala Glu Ala
                1060                1065                1070

Gly Asn Glu Ala Glu Asp Phe Gly Lys Lys Leu Lys Glu Ala Leu Asp
            1075                1080                1085

Ala Asn Ser Val Asp Asp Ile Lys Ala Ala Ile Lys Glu Met Ser Asp
    1090                1095                1100

Ala Met Gln Phe Asp Ser Val Gln Asp Val Leu Asn Gly Asp Ile Phe
1105                1110                1115                1120

Asn Asn Thr Lys Asp Gln Val Ala Pro Leu Asn Asp Leu Leu Glu Lys
                1125                1130                1135

Met Ala Glu Gly Lys Ser Ile Ser Ala Asn Glu Ala Asn Thr Leu Ile
            1140                1145                1150

Gln Lys Asp Lys Glu Leu Ala Gln Ala Ile Ser Ile Glu Asn Gly Val
        1155                1160                1165

Val Lys Ile Asn Arg Asp Glu Val Ile Lys Gln Arg Lys Val Lys Leu
        1170                1175                1180

Asp Ala Tyr Asn Asp Met Val Thr Tyr Ser Asn Lys Leu Met Lys Thr
1185                1190                1195                1200

Glu Val Asn Asn Ala Ile Lys Thr Leu Asn Ala Asp Thr Leu Arg Ile
                1205                1210                1215

Asp Ser Leu Lys Lys Leu Arg Lys Glu Arg Lys Leu Asp Met Ser Glu
        1220                1225                1230

Ala Glu Leu Ser Asp Leu Glu Val Lys Ser Ile Asn Asn Val Ala Asp
        1235                1240                1245

Ala Lys Lys Glu Leu Lys Lys Leu Glu Glu Lys Met Leu Gln Pro Gly
    1250                1255                1260

Gly Tyr Ser Asn Ser Gln Ile Glu Ala Met Gln Ser Val Lys Ser Ala
1265                1270                1275                1280

Leu Glu Ser Tyr Ile Ser Ala Ser Glu Glu Ala Thr Ser Thr Gln Glu
            1285                1290                1295

Met Asn Lys Gln Ala Leu Val Glu Ala Gly Thr Ser Leu Glu Asn Trp
        1300                1305                1310

Thr Asp Gln Gln Glu Lys Ala Asn Glu Glu Thr Lys Thr Ser Met Tyr
        1315                1320                1325

Val Val Asp Lys Tyr Lys Glu Ala Leu Glu Lys Val Asn Ala Glu Ile
    1330                1335                1340

Asp Lys Tyr Asn Lys Gln Val Asn Asp Tyr Pro Lys Tyr Ser Gln Lys
1345                1350                1355                1360
```

-continued

```
Tyr Arg Asp Ala Ile Lys Lys Glu Ile Lys Ala Leu Gln Gln Lys Lys
            1365                1370                1375
Lys Leu Met Gln Glu Gln Ala Lys Leu Leu Lys Asp Gln Ile Lys Ser
        1380                1385                1390
Gly Asn Ile Thr Gln Tyr Gly Ile Val Thr Ser Thr Ser Ser Gly
    1395                1400                1405
Gly Thr Pro Ser Ser Thr Gly Gly Ser Tyr Ser Gly Lys Tyr Ser Ser
    1410                1415                1420
Tyr Ile Asn Ser Ala Ala Ser Lys Tyr Asn Val Asp Pro Ala Leu Ile
1425                1430                1435                1440
Ala Ala Val Ile Gln Gln Glu Ser Gly Phe Asn Ala Lys Ala Arg Ser
            1445                1450                1455
Gly Val Gly Ala Met Gly Leu Met Gln Leu Met Pro Ala Thr Ala Lys
        1460                1465                1470
Ser Leu Gly Val Asn Asn Ala Tyr Asp Pro Tyr Gln Asn Val Met Gly
    1475                1480                1485
Gly Thr Lys Tyr Leu Ala Gln Gln Leu Glu Lys Phe Gly Gly Asn Val
    1490                1495                1500
Glu Lys Ala Leu Ala Ala Tyr Asn Ala Gly Pro Gly Asn Val Ile Lys
1505                1510                1515                1520
Tyr Gly Gly Ile Pro Pro Phe Lys Glu Thr Gln Asn Tyr Val Lys Lys
            1525                1530                1535
Ile Met Ala Asn Tyr Ser Lys Ser Leu Ser Ser Ala Thr Ser Ser Ile
        1540                1545                1550
Ala Ser Tyr Tyr Thr Asn Asn Ser Ala Phe Arg Val Ser Ser Lys Tyr
    1555                1560                1565
Gly Gln Gln Glu Ser Gly Leu Arg Ser Ser Pro His Lys Gly Thr Asp
    1570                1575                1580
Phe Ala Ala Lys Ala Gly Thr Ala Ile Lys Ser Leu Gln Ser Gly Lys
1585                1590                1595                1600
Val Gln Ile Ala Gly Tyr Ser Lys Thr Ala Gly Asn Trp Val Val Ile
            1605                1610                1615
Lys Gln Asp Asp Gly Thr Val Ala Lys Tyr Met His Met Leu Asn Thr
        1620                1625                1630
Pro Ser Val Lys Ala Gly Gln Ser Val Lys Ala Gly Gln Thr Ile Gly
    1635                1640                1645
Lys Val Gly Ser Thr Gly Asn Ser Thr Gly Asn His Leu His Leu Gln
    1650                1655                1660
Ile Glu Gln Asn Gly Lys Thr Ile Asp Pro Glu Lys Tyr Met Gln Gly
1665                1670                1675                1680
Ile Gly Thr Ser Ile Ser Asp Ala Ser Gln Ala Glu Ala Glu Arg Gln
            1685                1690                1695
Gln Gly Ile Ala Gln Ala Lys Ser Asp Leu Leu Ser Leu Gln Gly Asp
        1700                1705                1710
Ile Ser Ser Val Asn Asp Gln Ile Gln Glu Leu Gln Tyr Glu Leu Val
    1715                1720                1725
Gln Ser Lys Leu Asp Glu Phe Asp Lys Arg Ile Gly Asp Phe Asp Val
    1730                1735                1740
Arg Ile Ala Lys Asp Glu Ser Met Ala Asn Arg Tyr Thr Ser Asp Ser
1745                1750                1755                1760
Lys Glu Phe Arg Lys Tyr Thr Ser Asp Gln Lys Lys Ala Val Ala Glu
            1765                1770                1775
Gln Ala Lys Ile Gln Gln Gln Lys Val Asn Trp Ile Gln Lys Glu Ile
```

-continued

```
                 1780                1785                1790
Lys Thr Asn Lys Ala Leu Asn Ser Ala Gln Arg Ala Gln Leu Gln Glu
        1795                1800                1805

Glu Leu Lys Gln Ala Lys Leu Asp Leu Ile Ser Val Gln Asp Gln Val
    1810                1815                1820

Arg Glu Leu Gln Lys Gln Leu Val Gln Ser Lys Val Asp Glu Thr Leu
1825                1830                1835                1840

Lys Ser Ile Glu Lys Ser Ser Lys Thr Gln Gly Lys Ile Lys Asp
            1845                1850                1855

Val Asp Asn Lys Ile Ser Met Thr Glu Glu Asp Glu Asp Lys Val Lys
        1860                1865                1870

Tyr Tyr Ser Lys Gln Ile Lys Leu Ile Gln Gln Gln Lys Glu Ala
    1875                1880                1885

Lys Lys Tyr Ile Lys Gln Leu Glu Glu Gln Lys Lys Ala Ala Lys Gly
        1890                1895                1900

Phe Pro Asp Ile Gln Glu Gln Ile Thr Glu Met Gln Asn Trp Lys
1905                1910                1915                1920

Asp Lys Gln Lys Asp Phe Asn Leu Glu Leu Tyr Asn Thr Lys Lys Ser
            1925                1930                1935

Ile Lys Asp Ile Tyr Lys Ser Leu Ala Asp Glu Val Val Ser Ile Tyr
        1940                1945                1950

Lys Glu Met Tyr Glu Lys Met Arg Asp Ile Glu Leu Glu Ala His Gln
    1955                1960                1965

Lys Ala Thr Gln Asp Leu Ile Asp Glu Ile Asp Lys Thr Asp Asp Glu
    1970                1975                1980

Ala Lys Phe Gln Lys Glu Leu Lys Glu Arg Gln Asp Ser Ile Gln Lys
1985                1990                1995                2000

Leu Thr Asp Gln Ile Asn Gln Tyr Ser Leu Asp Asp Ser Glu Phe Gly
            2005                2010                2015

Lys Ser Lys Val Lys Glu Leu Thr Glu Gln Leu Gln Lys Glu Gln Leu
        2020                2025                2030

Asp Leu Asp Asp Phe Leu Lys Asp Arg Glu Ser Asn Lys Arg Lys Glu
            2035                2040                2045

Ala Leu Gln Asp Gln Leu Glu Lys Asp Glu Glu Ser Ile Asn Asn Lys
    2050                2055                2060

Tyr Asp Asn Leu Val Asn Asp Glu Arg Ala Phe Lys Lys Leu Glu Asp
2065                2070                2075                2080

Lys Ile Met Asn Gly Lys Ile Thr Asp Ile Ala Lys Gln Leu Asn Glu
            2085                2090                2095

Phe Ser Lys Phe Ile Asn Thr Asn Met Glu Ser Ile Gly Lys Ser Ile
                2100                2105                2110

Ser Asn Asn Leu Ile Asp Lys Leu Lys Glu Ala Ser Asn Ala Leu Asn
            2115                2120                2125

Thr Ala Val Lys Gly Asn Thr Thr Gly Lys Lys Val Ser Ser Phe Ala
    2130                2135                2140

Ser Gly Gly Tyr Thr Gly Thr Gly Leu Gly Ala Gly Lys Leu Ala Phe
2145                2150                2155                2160

Leu His Asp Lys Glu Leu Ile Leu Asn Lys Thr Asp Thr Ala Asn Ile
            2165                2170                2175

Leu Asp Thr Val Lys Ala Val Arg Glu Thr Ala Val Asp Asp Ser Pro
        2180                2185                2190

Lys Trp Gly Gln Gly Val Lys Leu Ala Asp Leu Ile Lys Lys Gly Ile
    2195                2200                2205
```

```
Thr Ser Ile Pro Ser Leu Val Pro Asn Val Asn Gln Ser Met Leu Thr
    2210                2215                2220

Asn Ser Leu Ile Pro Asn Leu Lys Lys Ile Glu Ile Pro Ser Lys Thr
2225                2230                2235                2240

Ile Ala Ser Ser Gly Asp Lys Thr Ile Asn Leu Thr Asn Thr Phe His
                2245                2250                2255

Ile Asp Lys Leu Ile Gly Gly Glu Ser Gly Ala Arg Ser Met Phe Glu
            2260                2265                2270

Ser Ile Lys Asn Glu Val Val Lys Leu Asn Gly Ser Met
        2275                2280                2285
```

<210> SEQ ID NO 3
<211> LENGTH: 316
<212> TYPE: PRT
<213> ORGANISM: Pseudomonas

<400> SEQUENCE: 3

```
Pro Lys Val Leu Leu Thr Leu Met Val Met Gln Ser Gly Pro Leu Gly
 1               5                  10                  15

Ala Pro Asp Glu Arg Ala Leu Ala Pro Leu Gly Arg Leu Ser Ala
             20                  25                  30

Lys Arg Gly Phe Asp Ala Gln Val Arg Asp Val Leu Gln Gln Leu Ser
         35                  40                  45

Arg Arg Tyr Tyr Gly Phe Glu Glu Tyr Gln Leu Arg Gln Ala Ala Ala
     50                  55                  60

Arg Lys Ala Val Gly Glu Asp Gly Leu Asn Ala Ala Ser Ala Ala Leu
 65                  70                  75                  80

Leu Gly Leu Leu Arg Glu Gly Ala Lys Val Ser Ala Val Gln Gly Gly
                 85                  90                  95

Asn Pro Leu Gly Ala Tyr Ala Gln Thr Phe Gln Arg Leu Phe Gly Thr
            100                 105                 110

Pro Ala Ala Glu Leu Leu Gln Pro Ser Asn Arg Val Ala Arg Gln Leu
        115                 120                 125

Gln Ala Lys Ala Ala Leu Ala Pro Pro Ser Asn Leu Met Gln Leu Pro
130                 135                 140

Trp Arg Gln Gly Tyr Ser Trp Gln Pro Asn Gly Ala His Ser Asn Thr
145                 150                 155                 160

Gly Ser Gly Tyr Pro Tyr Ser Ser Phe Asp Ala Ser Tyr Asp Trp Pro
                165                 170                 175

Arg Trp Gly Ser Ala Thr Tyr Ser Val Val Ala Ala His Ala Gly Thr
            180                 185                 190

Val Arg Val Leu Ser Arg Cys Gln Val Arg Val Thr His Pro Ser Gly
        195                 200                 205

Trp Ala Thr Asn Tyr Tyr His Met Asp Gln Ile Gln Val Ser Asn Gly
    210                 215                 220

Gln Gln Val Ser Ala Asp Thr Lys Leu Gly Val Tyr Ala Gly Asn Ile
225                 230                 235                 240

Asn Thr Ala Leu Cys Glu Gly Gly Ser Ser Thr Gly Pro His Leu His
                245                 250                 255

Phe Ser Leu Leu Tyr Asn Gly Ala Phe Val Ser Leu Gln Gly Ala Ser
            260                 265                 270

Phe Gly Pro Tyr Arg Ile Asn Val Gly Thr Ser Asn Tyr Asp Asn Asp
        275                 280                 285

Cys Arg Arg Tyr Tyr Phe Tyr Asn Gln Ser Ala Gly Thr Thr His Cys
```

-continued

```
              290                 295                 300
Ala Phe Arg Pro Leu Tyr Asn Pro Gly Leu Ala Leu
305                 310                 315
```

PROTEASES FROM GRAM-POSITIVE ORGANISMS

This is a Divisional of U.S. patent application Ser. No. 09/932,183, now U.S. Pat. No. 6,833,265, filed on Aug. 17, 2001, which is a Continuation of U.S. patent application Ser. No. 09/308,375, filed on May 14, 1999, now issued U.S. Pat. No. 6,300,117, which claims priority to PCT/US98/18828, filed Sep. 8, 1998.

FIELD OF THE INVENTION

The present invention relates to metallo-proteases derived from gram-positive microorganisms. The present invention provides nucleic acid and amino acid sequences of a metallo-protease identified in *Bacillus subtilis*. The present invention also provides methods for the production of the protease in host cells as well as the production of heterologous proteins in a host cell having a mutation or deletion of part or all of the proteases of the present invention.

BACKGROUND OF THE INVENTION

Gram-positive microorganisms such as members of the group *Bacillus*, have been used for large-scale industrial fermentation due, in part, to their ability to secrete their fermentation products into the culture media. In gram-positive bacteria, secreted proteins are exported across a cell membrane and a cell wall, and then are subsequently released into the external media usually maintaining their native conformation.

Various gram-positive microorganisms are known to secrete extracellular and/or intracellular protease at some stage in their life cycles. Many proteases are produced in large quantities for industrial purposes. A negative aspect of the presence of proteases in gram-positive organisms is their contribution to the overall degradation of secreted heterologous or foreign proteins.

The classification of proteases found in microorganisms is based on their catalytic mechanism which results in four groups: the serine proteases; metallo-proteases; cysteine proteases; and aspartic proteases. These categories, in general, can be distinguished by their sensitivity to various inhibitors. For example, the serine proteases are inhibited by phenylmethylsulfonylfluoride (PMSF) and diisopropylfluorophosphate (DIFP); the metallo-proteases by chelating agents; the cysteine enzymes by iodoacetamide and heavy metals and the aspartic proteases by pepstatin. The serine proteases have alkaline pH optima, the metalloproteases are optimally active around neutrality, and the cysteine and aspartic enzymes have acidic pH optima (*Biotechnology Handbooks, Bacillus*. vol. 2, edited by Harwood, 1989 Plenum Press, New York).

Metallo-proteases form the most diverse of the catalytic types of proteases. Family M23 contains bacterial enzymes such as the β-lytic endopeptidases of *Lysobacter* and *Achromobacter* and the *Pseudomonas* LasA protein and have specificity for Gly bonds, especially in Gly-Gly+Xaa-sequences (Methods in Enzymology, vol. 248, Academic Press, Inc. 1994). The enzymes of the M23 family contain zinc and a conserved His-Xaa-His motif

SUMMARY OF THE INVENTION

The present invention relates to the discovery of a heretofore unknown metallo-protease (MT) found in gram positive microorganisms, uses of the MP in industrial applications, and advantageous strain improvements based on genetically engineering such microorganisms to delete, underexpress or overexpress that MP. Due to the overall relatedness of MP with *Pseudomonas* lasA protein, including the presence of the motif His-Xaa-His, MP appears to be a member of the metallo-protease family M23.

Applicant's discovery, in addition to providing a new and useful protease and methods of detecting DNA encoding such proteases in a gram positive microorganism, provides several advantages which may facilitate optimization and/or modification of strains of gram positive microorganisms, such as *Bacillus*, for expression of desired, e.g. heterologous, proteins. Such optimizations, as described below in detail, allow the construction of strains having decreased proteolytic degradation of desired expression products.

Applicant's invention is further based on the discovery of the presence of MP's in Gram-positive microorganisms. The Gram-positive microorganism may be *Bacillus* and may also be selected from the group consisting of *Bacillus subtilis, Bacillus stearothermophilus, Bacillus licheniformis* and *Bacillus amyloliquifaciens*. The present invention further relies on the discovery that naturally occurring MP is encoded by nucleic acid found about 2248 kb from the point of origin of *Bacillus subtilis* I-168 strain (*Bacillus* Genetic Stock Center, accession number 1A1, Columbus, Ohio). The present invention relates to the MP encoded thereby, as well as the nucleic acid and amino acid molecules having the sequences disclosed in FIGS. 1A–1O (SEQ ID NOs:1 and 2).

The present invention thus provides methods for detecting gram positive microorganism homologs of *B. subtilis* MP that comprises hybridizing part or all of the nucleic acid encoding *B. subtilis* MP with nucleic acid derived from gram-positive organisms, either of genomic or cDNA origin. Accordingly, the present invention provides a method for detecting a gram-positive microorganism MP, comprising the steps of hybridizing gram-positive microorganism nucleic acid under low stringency conditions to a probe, wherein the probe comprises part or all of the nucleic acid sequence shown in FIGS. 1A–1O (SEQ ID NO:1); and isolating gram-positive nucleic acid which hybridizes to said probe.

In a preferred embodiment, the *Bacillus* is selected from the group consisting of *B. licheniformis, B. lentus, B. brevis, B. stearothermophilus, B. alkalophilus, B. amyloliquefaciens, B. coagulans, B. circulans, B. lautus* and *B. thuringiensis*.

The production of desired heterologous proteins or polypeptides in gram-positive microorganisms may be hindered by the presence of one or more proteases, including MP, which degrade the produced heterologous protein or polypeptide. One advantage of the present invention is that it provides methods and expression systems which can be used to prevent that degradation, thereby enhancing yields of the desired heterologous protein or polypeptide. Accordingly, the present invention provides a gram-positive microorganism having a mutation or deletion of part or all of the gene encoding MP, which results in the inactivation of the MP proteolytic activity, either alone or in combination with mutations in other proteases, such as apr, npr, epr, mpr, bpf or isp for example, or other proteases known to those of skill in the art. In one embodiment of the present invention, the gram-positive organism is a member of the genus *Bacillus*. In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and

*Bacillus thuringiensis.* In a further preferred embodiment, the *Bacillus* is *Bacillus subtilis.*

In another aspect, the gram-positive host having one or more metallo-protease deletions or mutations is further genetically engineered to produce a desired protein. In one embodiment of the present invention, the desired protein is heterologous to the gram-positive host cell. In another embodiment, the desired protein is homologous to the host cell. The present invention encompasses a gram-positive host cell having a deletion, mutation or interruption of the nucleic acid encoding the naturally occurring homologous protein, such as a protease, and having nucleic acid encoding the homologous protein re-introduced in a recombinant form. In another embodiment, the host cell produces the homologous protein. Accordingly, the present invention also provides methods and expression systems for reducing degradation of heterologous proteins produced in gram-positive microorganisms. The gram-positive microorganism may be normally sporulating or non-sporulating. In a preferred embodiment, the gram positive host cell is a *Bacillus.* In another preferred embodiment, the *Bacillus* host cell is *Bacillus.* In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *Bacillus thuringiensis.*

Naturally occurring gram positive MP as well as proteolytically active amino acid variations or derivatives thereof, have application in the textile industry, in cleaning compositions and in animal feed. The metallo-protease MP may be used alone or in combination with other enzymes and/or mediators or enhancers. Accordingly, in a further aspect of the present invention, gram-positive MP is produced on an industrial fermentation scale in a microbial host expression system. The present invention provides a cleaning to composition comprising a metalloprotease, MP, having the amino acid sequence shown in FIGS. 1A–1O (SEQ ID NO:2) or the amino acid encoded by the MP nucleic acid found at about 2248 kilobases from the point of origin of *Bacillus subtilis.* Also provided are cleaning compositions comprising a metalloprotease having at least 80%, at least 90%, or at least 95% homology with the amino acid sequence shown in FIGS. 1A–1O (SEQ ID NO:2) or comprising a metalloprotease encoded by a gene that hybridizes with the nucleic acid shown in FIGS. 1A–1O (SEQ ID NO:1) under high stringency conditions.

Further there is provided an animal feed comprising a metalloprotease, MP, having the amino acid sequence shown in FIGS. 1A–1O (SEQ ID NO:2). Also provided are animal feeds comprising a metalloprotease having at least 80%, at least 90%, and at least 95% homology with the amino acid sequence shown in FIGS. 1A–1O (SEQ ID NO:2) or comprising a metalloprotease encoded by a gene that hybridizes with the nucleic acid shown in FIGS. 1A–1O (SEQ ID NO:1) under high stringency conditions.

Also provided is a composition for the treatment of a textile comprising a metalloprotease, MP, having the amino acid sequence shown in FIGS. 1A–1O (SEQ ID NO:2). Also provided are compositions for the treatment of a textile comprising a metalloprotease having at least 80%, at least 90%, or at least 95% homology with the amino acid sequence shown in FIGS. 1A–1O (SEQ ID NO:2) or comprising a metalloprotease encoded by a gene that hybridizes with the nucleic acid shown in FIGS. 1A–1O (SEQ ID NO:1) under high stringency conditions.

BRIEF DESCRIPTION OF THE DRAWINGS

FIGS. 1A–1O shows the DNA (SEQ ID NO:1) and amino acid sequence (SEQ ID NO:2) for *Bacillus subtilis* MP.

FIG. 2 shows an amino acid alignment of *Bacillus subtilis* MP (designated as YOMI) and *Pseudomonas* LasA (SEQ ID NO:3). The amino acid motif H-X-H is noted at amino acid 308–310 in LasA

DETAILED DESCRIPTION OF THE PREFERRED EMBODIMENTS

Definitions

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus* and *B. thuringiensis.*

The present invention relates to a newly characterized metallo-protease (MP) from gram positive organisms. In a preferred embodiment, the metallo-protease is obtainable from a gram-positive organism which is a *Bacillus.* In another preferred embodiment, the metallo-protease is obtainable from a *Bacillus* which is selected from the group consisting of *B. subtilis, B. licheniformis, B. lentus, B. brevis, B. stearothermophilus, B. alkalophilus, B. amyloliquefaciens, B. coagulans, B. ciculans, B. lautus* and *B. thuringiensis.*

In another preferred embodiment, the gram-positive organism is *Bacillus subtilis* and MP has the amino acid sequence encoded by the nucleic acid molecule having the sequence that occurs around 2248 kilobases from the point of origin of *Bacillus subtilis* I-168.

In another preferred embodiment, *Bacillus subtilis* has the nucleic acid and amino acid sequence as shown in FIGS. 1A–1O (SEQ ID NOs:1 and 2, respectively). The present invention encompasses the use of amino acid variations of the amino acid sequences disclosed in FIGS. 1A–1O (SEQ ID NO:2) that have proteolytic activity. Such proteolytic amino acid variants can be used in the textile industry, animal feed and in cleaning compositions. The present invention also encompasses the use of *B. subtilis* amino acid variations or derivatives that are not proteolytically active. DNA encoding such variants can be used in methods designed to delete or mutate the naturally occurring host cell MP.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof A "polynucleotide homolog" as used herein refers to a gram-positive microorganism polynucleotide that has at least 80%, at least 90% and at least 95% identity to *B. subtilis* MP, or which is capable of hybridizing to *B. subtilis* MP under conditions of high stringency and which encodes an amino acid sequence having metallo-protease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases; cellulases, amylases, carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

As used herein, the term "overexpressing" when referring to the production of a protein in a host cell means that the protein is produced in greater amounts than its production in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

DETAILED DESCRIPTION OF THE PREFERRED EMBODIMENTS

The unexpected discovery of the metallo-protease M23 family member, designated herein as MP, found in translated, uncharacterized *B. subtilis* genomic sequences provides a basis for producing host cells, expression methods and systems which can be used to prevent the degradation of recombinantly produced heterologous proteins.

Accordingly, in a preferred embodiment, the host cell is a gram-positive host cell that has a deletion or mutation in the naturally occurring nucleic acid encoding MP said mutation resulting in deletion or inactivation of the production by the host cell of the MN proteolytic gene product. The host cell may additionally be genetically engineered to produced a desired protein or polypeptide.

It may also be desired to genetically engineer host cells of any type to produce a gram-positive MP. Such host cells are used in large scale fermentation to produce large quantities of the protease which may be isolated or purified and used in cleaning products, such as detergents, in textile treatments and as animal feed additives.

I. MP Sequences

The nucleic acid sequence and amino acid sequence for *Bacillus subtilis* MP are shown in FIGS. 1A–1O (SEQ ID NOS:1 and 2, respectively). As will be understood by the skilled artisan, due to the degeneracy of the genetic code, a variety of polynucleotides can encode the *Bacillus subtilis* MP having the amino acid sequence shown in FIGS. 1A–1O (SEQ ID NO:2). The present invention encompasses all such polynucleotides.

The present invention encompasses the use of MP polynucleotide homologs encoding gram-positive microorganism MPs which have at least 80%, or at least 90% or at least 95% identity to *B. subtilis* MP shown in FIGS. 1A–1O (SEQ ID NO:1) as long as the homolog encodes a protein that has proteolytic activity.

Gram-positive polynucleotide homologs of *B. subtilis* MP may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA.

As will be understood by those of skill in the art, the polynucleotide sequence disclosed in FIGS. 1A–1O (SEQ ID NO:1) may reflect inadvertent errors inherent to nucleic acid sequencing technology. Moreover, the sequence of polynucleotides derived from related species, e.g., other *Bacillus*, will contain variations to the sequences specifically disclosed herein. Nonetheless, one of ordinary skill in the art is fully capable of determining the correct sequences from the information provided herein regarding the invention. For example, as described below, it is possible to identify the MP of the invention by virtue of its location in the microorganism's genome. The present invention encompasses the naturally occurring nucleic acid molecule having the nucleic acid, sequence obtained from the genomic sequence of *Bacillus* species.

Nucleic acid encoding *Bacillus subtilis* MP starts around 2248 kilobases counting from the point of origin in the *Bacillus subtilis* strain I-168 (Anagnostopala, 1961, J. Bacteriol. 81:741–746 or *Bacillus* Genomic Stock Center, accession 1A1, Columbus, Ohio). The *Bacillus subtilis* point of origin has been described in Ogasawara, N. (1995, Microbiology 141:Pt.2 257–59). *Bacillus subtilis* MP has a length of 2285 amino acids. Based upon the location of the DNA encoding *Bacillus subtilis* MP, naturally occurring *B. subtilis* MP can be obtained by methods known to those of skill in the art including PCR technology.

Oligonucleotide sequences or primers of about 10–30 nucleotides in length can be designed from the polynucleotide sequence disclosed in FIGS. 1A–1O (SEQ ID NO:1) and used in PCR technology to isolate the naturally occurring sequence from *B. subtilis* genomic sequences.

Another general strategy for the "cloning" of *B. subtilis* genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned" DNA pieces. From the most external DNA sequence a new round of inverse PCR is started. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.).

Nucleic acid sequences derived from genomic DNA may contain regulatory regions in addition to coding regions. Whatever the source, the isolated MP gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the MP may be accomplished in a number of ways. For example, a *B. subtilis* MP gene of the present invention, or its specific RNA, or a fragment thereof, such as a probe or primer, may be isolated and labeled and then used in hybridization assays to detect a gram-positive MP gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram-positive MP polynucleotide homologs which comprises hybridizing part or all of a nucleic acid sequence of *B. subtilis* MP with gram-positive microorganism nucleic acid of either genomic or cDNA origin.

Also included within the scope of the present invention is the use of gram-positive microorganism polynucleotide sequences that are capable of hybridizing to the nucleotide sequence of *B. subtilis* MP under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*, Vol 152, Academic Press, San Diego Calif.) incorporated herein by reference and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from *B. subtilis* MP preferably about 12 to 30 nucleotides, and more preferably about 20–25 nucleotides can be used as a probe or PCR primer.

The *B. subtilis* MP amino acid sequence (shown in FIGS. 1A–1O (SEQ ID NO:2) was identified via a BLAST search (Altschul, Stephen, Basic local alignment search tool, J. Mol. Biol. 215:403–410) of *Bacillus subtilis* genomic nucleic acid sequences. *B. subtilis* MP (YOMI) was identified by its overall nucleic acid identity to the metallo-protease, *Pseudomonas* lasA (SEQ ID NO:3) including the presence of the catalytic domain H-X-H as shown in FIG. 2.

II. Expression Systems

The present invention provides host cells, expression methods and systems for the enhanced production and secretion of desired heterologous or homologous proteins in gram-positive microorganisms. In one embodiment, a host cell is genetically engineered to have a deletion or mutation in the gene encoding a gram-positive MP such that the respective activity is deleted. In another embodiment of the present invention, a gram-positive microorganism is genetically engineered to produce a metallo-protease of the present invention.

Inactivation of a Gram-Positive Metallo-Protease in a Host Cell

Producing an expression host cell incapable of producing the naturally occurring metallo-protease necessitates the replacement and/or inactivation of the naturally occurring gene from the genome of the host cell. In a preferred embodiment, the mutation is a non-reverting mutation.

One method for mutating nucleic acid encoding a gram-positive metallo-protease is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the metallo-protease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded metallo-protease gene. In another preferred embodiment, nucleic acid encoding the catalytic amino acid residues are deleted.

Deletion of the naturally occurring gram-positive microorganism metallo-protease can be carried out as follows. A metallo-protease gene including its 5' and 3' regions is isolated and inserted into a cloning vector. The coding region of the metallo-protease gene is deleted form the vector in vitro, leaving behind a sufficient amount of the 5' and 3' flanking sequences to provide for homologous recombination with the naturally occurring gene in the parent host cell. The vector is then transformed into the gram-positive host cell. The vector integrates into the chromosome via homologous recombination in the flanking regions. This method leads to a gram-positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the metallo-protease locus. Since illegitimate recombination will give different results it will be necessary to determine whether the complete gene has been deleted, such as through nucleic acid sequencing or restriction maps.

Another method of inactivating the naturally occurring metallo-protease gene is to mutagenize the chromosomal gene copy by transforming a gram-positive microorganism with oligonucleotides which are mutagenic. Alternatively, the chromosomal metallo-protease gene can be replaced with a mutant gene by homologous recombination.

The present invention encompasses host cells having additional protease deletions or mutations, such as deletions or mutations in apr, npr, epr, mpr and others known to those of skill in the art.

One assay for the detection of mutants involves growing the *Bacillus* host cell on medium containing a protease substrate and measuring the appearance or lack thereof, of a zone do clearing or halo around the colonies. Host cells which have an inactive protease will exhibit little or no halo around the colonies.

III. Production of Metallo-Protease

For production of metallo-protease in a host cell, an expression vector comprising at least one copy of nucleic acid encoding a gram-positive microorganism MP, and preferably comprising multiple copies, is transformed into the host cell under conditions suitable for expression of the metallo-protease. In accordance with the present invention, polynucleotides which encode a gram-positive microorganism MP, or fragments thereof, or fusion proteins or polynucleotide homolog sequences that encode amino acid variants of *B. subtilis* MP, may be used to generate recombinant DNA molecules that direct their expression in host cells. In a preferred embodiment, the gram-positive host cell belongs to the genus *Bacillus*. In another preferred embodiment, the gram positive host cell is *B. subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered MP polynucleotide sequences which may be used in accordance with the invention include deletions, insertions or substitutions of different nucleotide residues resulting in a polynucleotide that encodes the same or a functionally equivalent MP homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring MP.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent MP variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The MP polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a gram-positive microorganism MP polynucleotide may be ligated to a heterologous sequence to encode a fusion protein. A fusion protein may also be engineered to contain a cleavage site located between the metallo-protease nucleotide sequence and the heterologous protein sequence, so that the metallo-protease may be cleaved and purified away from the heterologous moiety.

IV. Vector Sequences

Expression vectors used in expressing the metallo-proteases of the present invention in gram-positive microorganisms comprise at least one promoter associated with a metallo-protease selected from the group consisting of MP, which promoter is functional in the host cell. In one embodiment of the present invention, the promoter is the wild-type promoter for the selected metallo-protease and in another embodiment of the present invention, the promoter is heterologous to the metallo-protease, but still functional in the host cell. In one preferred embodiment of the present invention, nucleic acid encoding the metallo-protease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production *Bacillus subtilis* MP or MP homologs including bacterial, fungal, mammalian and insects cells. General transformation procedures are taught in Current Protocols In Molecular Biology (vol. 1, edited by Ausubel et al., John Wiley & Sons, Inc. 1987, Chapter 9) and include calcium phosphate methods, transformation using DEAE-Dextran and electroporation. Plant transformation methods are taught in Rodriquez (WO 95/14099, published 26 May 1995).

In a preferred embodiment, the host cell is a gram-positive microorganism and in another preferred embodiment, the host cell is *Bacillus*. In one embodiment of the present invention, nucleic acid encoding one or more MP(s) of the present invention is introduced into a host cell via an expression vector capable of replicating within the *Bacillus* host cell. Suitable replicating plasmids for *Bacillus* are described in Molecular Biological Methods for *Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, where it is desired to produce the MP for use in cleaning compositions, nucleic acid encoding MP is stably integrated into the microorganism genome. Preferred host cells are gram-positive host cells. Another preferred host is *Bacillus*. Another preferred host is *Bacillus subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., Plasmid 2:555–571 (1979); Haima et al., Mol. Gen. Genet. 223:185–191 (1990); Weinrauch et al., J. Bacteriol. 154(3):1077–1087 (1983); and Weinrauch et al., J. Bacteriol. 169(3):1205–1211 (1987)). The incoming donor plasmid recombines with the homologous region of the resident "helper" plasmid in a process that mimics chromosomal transformation.

Protoplast transformation is described for *B. subtilis* in Chang and Cohen, (1979) Mol. Gen. Genet 168:111–115; for *B. megaterium* in Vorobjeva et al., (1980) FEMS Microbiol. Letters 7:261–263; for *B. amyloliquefaciens* in Smith et al., (1986) Appl. and Env. Microbiol. 51:634, for *B. thuringiensis* in Fisher et al., (1981) Arch. Microbiol. 139: 213–217; for *B. sphaericus* in McDonald (1984) J. Gen. Microbiol. 130'203; and *B. larvae* in Bakhiet et al., (1985, Appl. Environ. Microbiol. 49:577). Mann et al., (1986, Current Microbiol. 13:131–135) report on transformation of *Bacillus* protoplasts and Holubova, (1985) Folia Microbiol. 30:97) disclose methods for introducing DNA into protoplasts using DNA containing liposomes.

VI. Identification of Transformants

Whether a host cell has been transformed with a mutated or a naturally occurring gene encoding a gram-positive MP, detection of the presence/absence of market gene expression can suggest whether the gene of interest is present However, its expression should be confirmed. For example, if the nucleic acid encoding an MP of the present invention is inserted within a marker gene sequence, recombinant cells containing the insert can be identified by the absence of marker gene function. Alternatively, a marker gene can be placed in tandem with nucleic acid encoding the MP under the control of a single promoter. Expression of the marker gene in response to induction or selection usually indicates expression of the MP as well.

Alternatively, host cells which contain the coding sequence for a metallo-protease and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the metallo-protease polynucleotide sequence can be detected by DNA-DNA or DNA-RNA hybridization or amplification using probes, portions or fragments of *B. subtilis* MP.

VII. Assay of Protease Activity

There are various assays known to those of skill in the art for detecting and measuring protease activity. There are assays based upon the release of acid-soluble peptides from casein or hemoglobin measured as absorbance at 280 nm or colorimetrically using the Folin method (Bergmeyer, et al., 1984, Methods of Enzymatic Analysis vol. 5, Peptidases, Proteinases and their Inhibitors, Verlag Chemie, Weinheim). Other assays involve the solubilization of chromogenic substrates (Ward, 1983, Proteinases, in Microbial Enzymes and Biotechnology (W. M, Fogarty, ed.), Applied Science, London, pp. 251–317).

VIII. Secretion of Recombinant Proteins

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the is art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a mutation or deletion of the metallo-protease activity will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention MP and Genetically Engineered Host Cells

The present invention provides genetically engineered host cells comprising mutations, preferably non-revertable mutations, or deletions in the naturally occurring gene encoding MP such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is further genetically engineered to produce a desired protein or polypeptide. In a preferred embodiment the host cell is a *Bacillus*. In another preferred embodiment, the host cell is a *Bacillus subtilis*.

In an alternative embodiment, a host cell is genetically engineered to produce a gram-positive MP. In a preferred embodiment, the host cell is grown under large scale fermentation conditions. In another preferred embodiment, the MP is isolated and/or purified and used in the textile industry, the feed industry and in cleaning compositions such as detergents.

As noted, MP can be useful in formulating various cleaning compositions. A number of known compounds are suitable surfactants useful in compositions comprising the MP of the invention. These include nonionic, anionic, cationic, anionic or zwitterionic detergents, as disclosed in U.S. Pat. No. 4,404,128 and U.S. Pat. No. 4,261,868. A suitable detergent formulation is that described in Example 7 of U.S. Pat. No. 5,204,015. The art is familiar with the different formulations which can be used as cleaning compositions. In addition, MP can be used, for example, in bar or liquid soap applications, dishcare formulations, contact lens cleaning solutions or products, peptide hydrolysis, waste treatment, textile applications, as fusion-cleavage enzymes in protein production, etc. MP may comprise enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

MP can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of MP to conventional cleaning compositions does not create any special use limitation. In other words, any temperature and pH suitable for the detergent is also suitable for the present compositions as long as the pH is within the above range, and the temperature is below the described MP's denaturing temperature. In addition, MP can be used in a cleaning composition without detergents, again either alone or in combination with builders and stabilizers.

In another aspect of the invention a metalloprotease of the invention can be included in animal feed such as components of compositions which are animal feed additives as described in, for example, U.S. Pat. No. 5,612,055; U.S. Pat. No. 5,314,692; and U.S. Pat. No. 5,147,642, wherein U.S. Pat. No. 5,612,055 discloses, in the abstract, that an animal feed may comprise an "enzyme feed additive . . . comprising a xylanase, a protease, and optionally a β-glucanase", and U.S. Pat. No. 5,314,692 discloses, in Example 1 at column 4, a livestock feed premix that comprises an "alpha-amylase", a "protease" and a cellulase while U.S. Pat. No. 5,147,642 discloses, in the abstract, that "bacteriolytic enzyme products and proteases can be added in a mixture as additive to feedstuffs".

In a further aspect of the invention a metalloprotease of the invention can be included in a composition for the treatment of a textile. The composition can be used to treat for example silk or wool as described in publications such as RD 216,034; EP 134,267; U.S. Pat. No. 4,533,359; and EP 344,259, wherein U.S. Pat. No. 4,533,359 discloses that treatment of animal textile fibers with a "proteolytic enzyme is preferably carried out in a saturated or nearly saturated aqueous solution of an inorganic salt" at column 2, lines 62–65.

MP Polynucleotides

A *B. subtlis* MP polynucleotide, or any part thereof, provides the basis for detecting the presence of gram-positive microorganism MP polynucleotide homologs through hybridization techniques and PCR technology.

Accordingly, one aspect of the present invention is to provide for nucleic acid hybridization and PCR probes which can be used to detect polynucleotide sequences, including genomic and cDNA sequences, encoding gram-positive MP or portions thereof. In another aspect of the present invention, an MP polynucleotide can be used in hybridization technology to detect the major protease of a gram-positive microorganism due to the proximity of the MP with the major protease.

The manner and method of carrying out the present invention may be more fully understood by those of skill in the art by reference to the following examples, which examples are not intended in any manner to limit the scope of the present invention or of the claims directed thereto

EXAMPLE I

Preparation of a Genomic Library

The following example illustrates the preparation of a *Bacillus* genomic library.

Genomic DNA from *Bacillus* cells is prepared as taught in Current Protocols In Molecular Biology vol. 1, edited by Ausubel et al., John Wiley & Sons, Inc. 1987, chapter 2. 4.1. Generally, *Bacillus* cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the *Bacillus* genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested *Bacillus* genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram-Positive Microorganisms

The following example describes the detection of gram-positive microorganism MP.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from MP.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1× saline sodium citrate and 0.5% sodium dodecyl sulfate. The blots are exposed to film for several hours, the film developed and hybridization patterns are compared visually to detect polynucleotide homologs of *B. subtilis* MP. The homologs are subjected to confirmatory nucleic acid sequencing. Methods for nucleic acid is sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

The invention claimed is:

1. A cleaning composition comprising a Gram-positive microorganism metalloprotease of *Bacillus subtilis*, and a surfactant, wherein said metalloprotease comprises the amino acid sequence set forth in SEQ ID NO:2.

2. The cleaning composition of claim 1 wherein said metalloprotease has the amino acid sequence encoded by the nucleic acid sequence set forth in SEQ ID NO:1.

3. An animal feed comprising a Gram-positive microorganism metalloprotease of *Bacillus subtilis*, and an animal feed additive selected from the group consisting of an animal feed enzyme premix, a bacteriolytic enzyme, a xylanase, a subtilisin protease, a cellulase and a β-glucanase, wherein said metalloprotease comprises the amino acid sequence set forth in SEQ ID NO:2.

4. A composition for the treatment of a textile comprising a Gram-positive microorganism metalloprotease of *Bacillus subtilis*, and an inorganic salt, wherein said metalloprotease comprises the amino acid sequence set forth in SEQ ID NO:2.

* * * * *